(12) United States Patent
Boudreaux et al.

(10) Patent No.: US 9,237,900 B2
(45) Date of Patent: Jan. 19, 2016

(54) SURGICAL INSTRUMENT WITH SPLIT JAW

(71) Applicant: Ethicon Endo-Surgery, Inc., Cincinnati, OH (US)

(72) Inventors: Chad P. Boudreaux, Cincinnati, OH (US); Aaron C. Voegele, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 395 days.

(21) Appl. No.: 13/891,804

(22) Filed: May 10, 2013

(65) Prior Publication Data

US 2014/0336698 A1    Nov. 13, 2014

(51) Int. Cl.
| | |
|---|---|
| *A61B 17/00* | (2006.01) |
| *A61B 17/28* | (2006.01) |
| *A61B 18/00* | (2006.01) |
| *A61B 18/14* | (2006.01) |
| *A61B 17/32* | (2006.01) |
| *A61B 17/29* | (2006.01) |

(52) U.S. Cl.
CPC ....... *A61B 17/282* (2013.01); *A61B 17/320092* (2013.01); *A61B 18/00* (2013.01); *A61B 18/1445* (2013.01); *A61B 18/1447* (2013.01); *A61B 2017/2926* (2013.01); *A61B 2017/2927* (2013.01); *A61B 2017/320096* (2013.01); *A61B 2018/1455* (2013.01)

(58) Field of Classification Search
CPC ..................... A61B 17/282; A61B 17/320092; A61B 18/1447; A61B 18/1445; A61B 2017/2927; A61B 2018/1455; A61B 2017/2926; A61B 2017/301; A61B 2017/303; A61B 10/06; A61B 17/1606; A61B 17/1608; A61B 2017/2932; A61B 17/2938; B25B 7/02; B25B 7/22; B25B 13/28; B25B 13/505
USPC ......... 81/302–308, 310, 90.1, 90.5, 342, 418, 81/419, 424; 294/104, 209, 86.4; 901/31; 606/169, 205–209
See application file for complete search history.

(56) References Cited

U.S. PATENT DOCUMENTS

| | | | | |
|---|---|---|---|---|
| 131,188 | A | * | 9/1872 | Sneider .............................. 86/40 |
| 1,334,657 | A | * | 3/1920 | Kent ................................. 81/9.3 |
| 3,106,035 | A | * | 10/1963 | Tennyson ....................... 43/53.5 |
| 4,805,823 | A | | 2/1989 | Rothfuss |
| 4,872,456 | A | * | 10/1989 | Hasson .......................... 606/207 |
| 5,354,110 | A | * | 10/1994 | Licata ............................. 294/11 |
| 5,415,334 | A | | 5/1995 | Williamson, IV et al. |
| 5,441,494 | A | * | 8/1995 | Ortiz ................................. 606/1 |
| 5,465,895 | A | | 11/1995 | Knodel et al. |
| 5,597,107 | A | | 1/1997 | Knodel et al. |

(Continued)

OTHER PUBLICATIONS

U.S. Appl. No. 61/410,603, filed Nov. 5, 2010.

(Continued)

*Primary Examiner* — Amy R Weisberg
(74) *Attorney, Agent, or Firm* — Frost Brown Todd LLC

(57) ABSTRACT

An apparatus for operating on tissue includes an end effector having a first jaw and a second jaw that pivots relative to the first jaw from a closed position to an open position. The second jaw includes a first portion and a second portion that pivots relative to the first portion. The second portion is positioned adjacent to the first portion of the second jaw when the second jaw is in the closed position. The first and second portions of the second jaw pivot outwardly as the second jaw is pivoted from the closed position to the open position.

20 Claims, 23 Drawing Sheets

(56) References Cited

U.S. PATENT DOCUMENTS

| | | | |
|---|---|---|---|
| 5,632,432 A | 5/1997 | Schulze et al. | |
| 5,673,840 A | 10/1997 | Schulze et al. | |
| 5,704,534 A | 1/1998 | Huitema et al. | |
| 5,776,075 A * | 7/1998 | Palmer | 600/564 |
| 5,814,055 A | 9/1998 | Knodel et al. | |
| 6,132,429 A * | 10/2000 | Baker | 606/50 |
| 6,500,176 B1 | 12/2002 | Truckai et al. | |
| 6,783,524 B2 | 8/2004 | Anderson et al. | |
| 6,978,921 B2 | 12/2005 | Shelton, IV et al. | |
| 7,000,818 B2 | 2/2006 | Shelton, IV et al. | |
| 7,112,201 B2 | 9/2006 | Truckai et al. | |
| 7,125,409 B2 | 10/2006 | Truckai et al. | |
| 7,143,923 B2 | 12/2006 | Shelton, IV et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,303,108 B2 | 12/2007 | Shelton, IV et al. | |
| 7,309,849 B2 | 12/2007 | Truckai et al. | |
| 7,311,709 B2 | 12/2007 | Truckai et al. | |
| 7,354,440 B2 | 4/2008 | Truckal et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,381,209 B2 | 6/2008 | Truckai et al. | |
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 7,997,468 B2 * | 8/2011 | Farascioni | 227/176.1 |
| 8,408,439 B2 | 4/2013 | Huang et al. | |
| 8,453,914 B2 | 6/2013 | Laurent et al. | |
| 8,461,744 B2 | 6/2013 | Wiener et al. | |
| 8,974,479 B2 * | 3/2015 | Ross et al. | 606/169 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2011/0082486 A1 | 4/2011 | Messerly et al. | |
| 2011/0087212 A1 | 4/2011 | Aldridge et al. | |
| 2011/0087213 A1 | 4/2011 | Messerly et al. | |
| 2011/0087214 A1 | 4/2011 | Giordano et al. | |
| 2011/0087215 A1 | 4/2011 | Aldridge et al. | |
| 2011/0087216 A1 | 4/2011 | Aldridge et al. | |
| 2011/0087217 A1 | 4/2011 | Yates et al. | |
| 2011/0087218 A1 | 4/2011 | Boudreaux et al. | |
| 2012/0078243 A1 | 3/2012 | Worrell et al. | |
| 2012/0078244 A1 | 3/2012 | Worrell et al. | |
| 2012/0078247 A1 | 3/2012 | Worrell et al. | |
| 2012/0078248 A1 | 3/2012 | Worrell et al. | |
| 2012/0083783 A1 | 4/2012 | Davison et al. | |
| 2012/0116379 A1 | 5/2012 | Yates et al. | |
| 2012/0239080 A1 * | 9/2012 | Fan | 606/205 |
| 2013/0023868 A1 | 1/2013 | Worrell et al. | |
| 2013/0030428 A1 | 1/2013 | Worrell et al. | |
| 2013/0085494 A1 * | 4/2013 | Weisenburgh et al. | 606/41 |
| 2014/0039512 A1 * | 2/2014 | He et al. | 606/110 |
| 2014/0074084 A1 * | 3/2014 | Engeberg et al. | 606/33 |
| 2015/0133980 A1 * | 5/2015 | Ross et al. | 606/169 |
| 2015/0150573 A1 * | 6/2015 | Van Tol et al. | 606/51 |
| 2015/0150581 A1 * | 6/2015 | Van Tol et al. | 606/51 |
| 2015/0150584 A1 * | 6/2015 | Van Tol et al. | 606/51 |

OTHER PUBLICATIONS

U.S. Appl. No. 61/410,603, filed Oct. 24, 2011.

* cited by examiner

SURGICAL INSTRUMENT WITH SPLIT JAW

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; U.S. Pub. No. 2012/0083783, entitled "Surgical Instrument with Jaw Member," published Apr. 5, 2012, now U.S. Pat. No. 8,888,809, issued Nov. 18, 2014, the disclosure of which is incorporated by reference herein; U.S. Pub. No. 2012/0116379, entitled "Motor Driven Electrosurgical Device with Mechanical and Electrical Feedback," published May 10, 2012, the disclosure of which is incorporated by reference herein; U.S. Pub. No. 2012/0078243, entitled "Control Features for Articulating Surgical Device," published Mar. 29, 2012, the disclosure of which is incorporated by reference herein; U.S. Pub. No. 2012/0078247, entitled "Articulation Joint Features for Articulating Surgical Device," published Mar. 29, 2012, the disclosure of which is incorporated by reference herein; U.S. Pub. No. 2013/0030428, entitled "Surgical Instrument with Multi-Phase Trigger Bias," published Jan. 31, 2013, now U.S. Pat. No. 9,089,327, issued Jul. 28, 2015, the disclosure of which is incorporated by reference herein; and U.S. Pub. No. 2013/0023868, entitled "Surgical Instrument with Contained Dual Helix Actuator Assembly," published Jan. 31, 2013, the disclosure of which is incorporated by reference herein.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
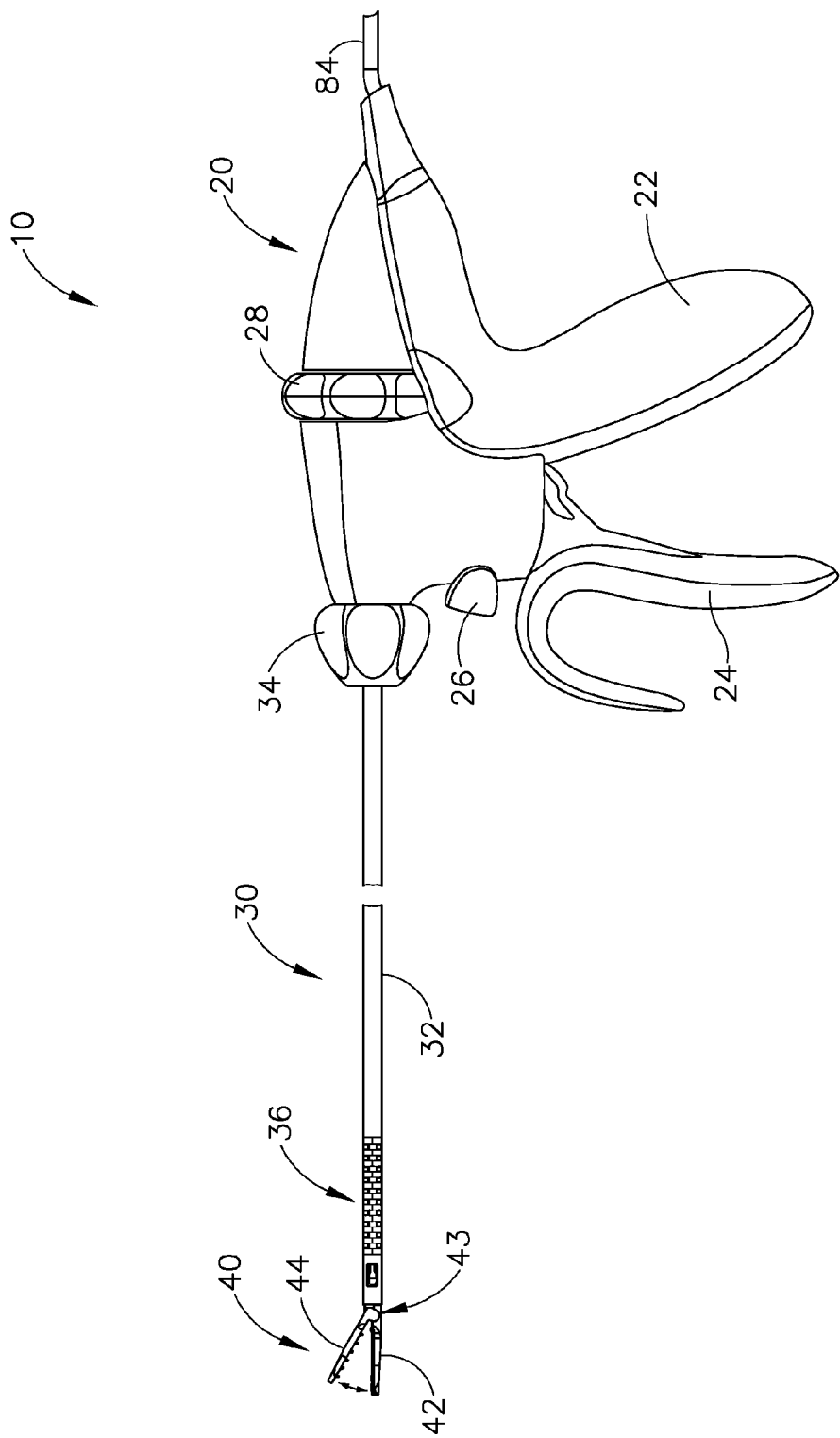
FIG. 1 depicts a side elevational view of an exemplary electrosurgical medical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Electrosurgical Device with Articulation Feature

FIGS. 1-4 show an exemplary electrosurgical instrument (10) that is constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pub. No. 2011/0087218, now U.S. Pat. No. 8,939,974; U.S. Pub. No. 2012/0083783, now U.S. Pat. No. 8,888,809; U.S. Pub. No.2012/0116379; U.S. Pub. No. 2012/0078243; U.S. Pub. No. 2012/0078247; U.S. Pub. No. 2013/0030428, now U.S. Pat. No. 9,089,327; and/or U.S. Pub. No. 2013/0023868. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. In addition or in the alternative, trigger (24) may serve as an electrical and/or mechanical lockout against button (26), such that button (26) cannot be effectively activated unless trigger (24) is being squeezed simultaneously. It should be understood that pistol grip (22), trigger (24), and button (26) may be modified, substituted, supplemented, etc. in any suitable way, and that the descriptions of such components herein are merely illustrative.

Shaft (30) of the present example includes a rigid outer sheath (32) and an articulation section (36). Articulation section (36) is operable to selectively laterally deflect end effector (40) at various angles relative to the longitudinal axis defined by sheath (32). In some versions, articulation section (36) and/or some other portion of outer sheath (32) includes a flexible outer sheath (e.g., a heat shrink tube, etc.) disposed about its exterior. Articulation section (36) of shaft (30) may take a variety of forms. By way of example only, articulation section (36) may be configured in accordance with one or more teachings of U.S. Pub. No. 2012/0078247, the disclosure of which is incorporated by reference herein. As another merely illustrative example, articulation section (36) may be configured in accordance with one or more teachings of U.S. Pub. No. 2012/0078248, entitled "Articulation Joint Features for Articulating Surgical Device," published Mar. 29, 2012, the disclosure of which is incorporated by reference herein. Various other suitable forms that articulation section (36) may take will be apparent to those of ordinary skill in the art in view of the teachings herein. It should also be understood that some versions of instrument (10) may simply lack articulation section (36).

In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating articulation section (36) or any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating articulation section (36) or any portion of shaft (30) that is proximal of articulation section (36). Other suitable rotation schemes will be apparent to those of ordinary skill in the art in view of the teachings herein. Of course, rotatable features may simply be omitted if desired.

Articulation control (28) of the present example is operable to selectively control articulation section (36) of shaft (30), to thereby selectively laterally deflect end effector (40) at various angles relative to the longitudinal axis defined by shaft (30). While articulation control (28) is in the form of a rotary dial in the present example, it should be understood that articulation control (28) may take numerous other forms. By way of example only, some merely illustrative forms that articulation control (28) and other components of handpiece (20) may take are disclosed in U.S. Pub. No. 2012/0078243, the disclosure of which is incorporated by reference herein; in U.S. Pub. No. 2012/0078244, entitled "Control Features for Articulating Surgical Device," published Mar. 29, 2012, the disclosure of which is incorporated by reference herein; and in U.S. Pub. No. 2013/0023868, the disclosure of which is incorporated by reference herein. Still other suitable forms that articulation control (28) may take will be apparent to those of ordinary skill in the art in view of the teachings herein. It should also be understood that some versions of instrument (10) may simply lack an articulation control (28).

B. Exemplary End Effector

End effector (40) of the present example comprises a first jaw (42) and a second jaw (44). In the present example, first jaw (42) is substantially fixed relative to shaft (30); while second jaw (44) pivots relative to shaft (30), toward and away from first jaw (42). Use of the term "pivot" should not be read as necessarily requiring pivotal movement about a fixed axis. In some versions, second jaw (44) pivots about an axis that is defined by a pin (or similar feature) that slides along an elongate slot or channel as second jaw (44) moves toward first jaw (42). In such versions, the pivot axis translates along the path defined by the slot or channel while second jaw (44) simultaneously pivots about that axis. It should be understood that such sliding/translating pivotal movement is encompassed within terms such as "pivot," "pivots," "pivotal," "pivotable," "pivoting," and the like. Of course, some versions may provide pivotal movement of second jaw (44) about an axis that remains fixed and does not translate within a slot or channel, etc.

In some versions, actuators such as rods or cables, etc., may extend through sheath (32) and be joined with second jaw (44) at a pivotal coupling (43), such that longitudinal movement of the actuator rods/cables/etc. through shaft (30) provides pivoting of second jaw (44) relative to shaft (30) and relative to first jaw (42). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
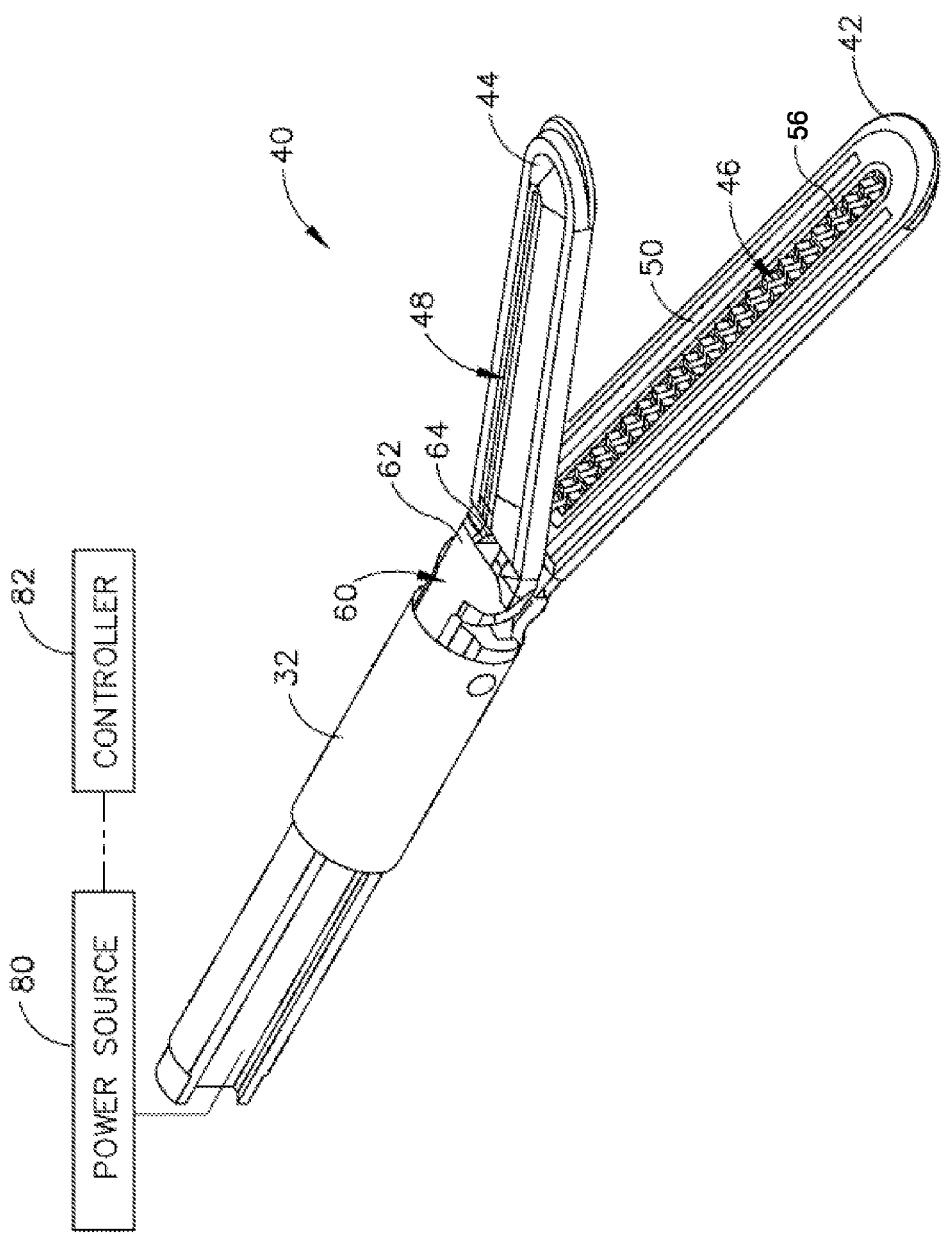
FIG. 2 depicts a perspective view of the end effector of the instrument of FIG. 1, in an open configuration.
Figure 3:
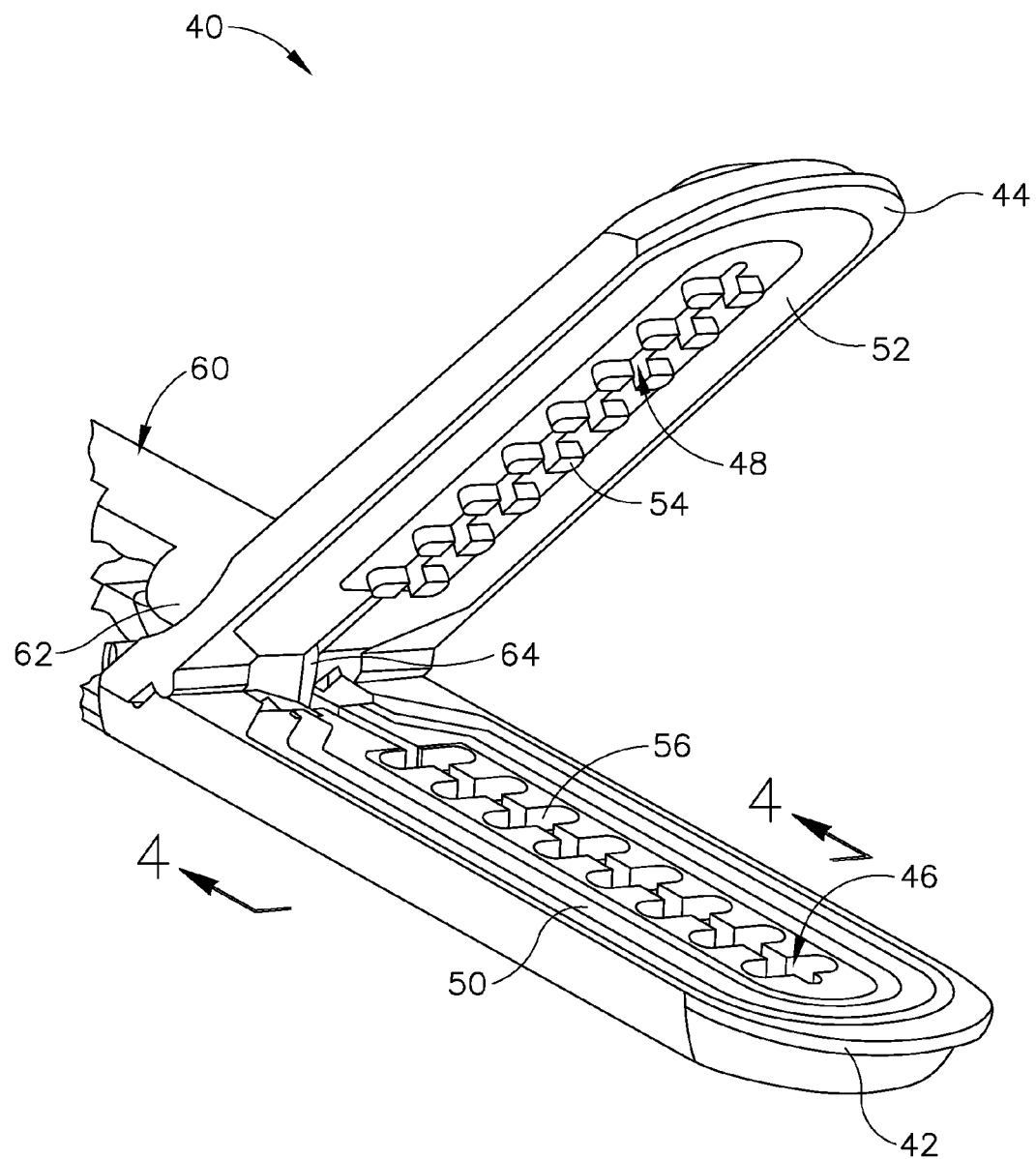
FIG. 3 depicts another perspective view of the end effector of the instrument of FIG. 1, in an open configuration.
Figure 4:
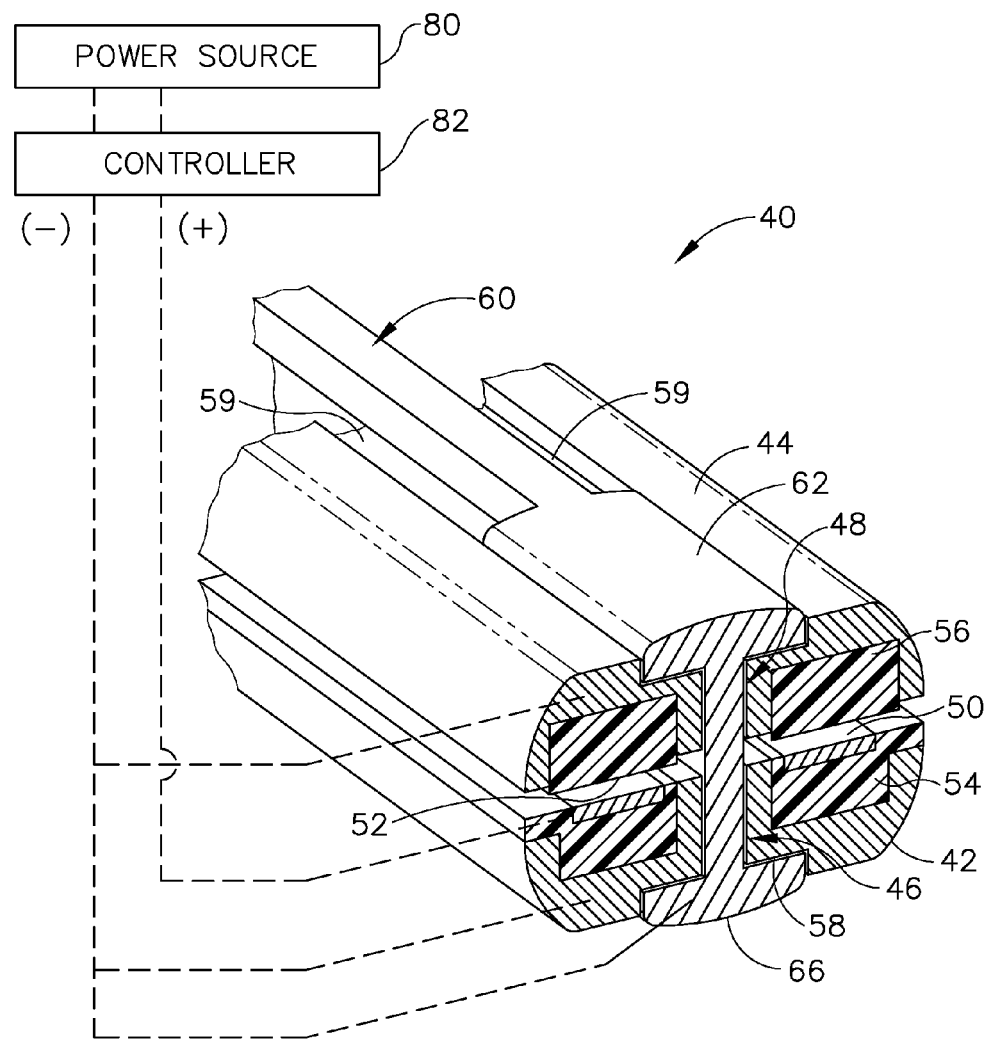
FIG. 4 depicts a cross-sectional end view of the end effector of FIG. 2, in a closed configuration and with the blade in a distal position, taken along line 4-4 of FIG. 3.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw (44) presents a second electrode surface (52). Electrode surfaces (50, 52) are in communication with an electrical source (80) via one or more conductors (not shown) that extend along the length of shaft (30). These conductors are coupled with electrical source (80) and a controller (82) via a cable (84), which extends proximally from handpiece (20). Electrical source (80) is operable to deliver RF energy to first electrode surface (50) at an active polarity while second electrode surface (52) serves as a reference/return passive electrode, such that RF current flows between electrode surfaces (50, 52) and thereby through tissue captured between jaws (42, 44). There are instances where the active signal crosses zero potential that the reference is at the same potential so there is no current flow. In some versions, firing beam (60) serves as an electrical conductor that cooperates with electrode surfaces (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

By way of example only, power source (80) and/or controller (82) may be configured in accordance with at least some of the teachings of U.S. Provisional Pat. App. No. 61/550,768, entitled "Medical Instrument," filed Oct. 24, 2011, the disclosure of which is incorporated by reference herein; U.S. Pub. No. 2011/0082486, entitled "Devices and Techniques for Cutting and Coagulating Tissue," published Apr. 7, 2011, now U.S. Pat. No. 9,089,360, issued Jul. 28, 2015, the disclosure of which is incorporated by reference herein; U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein; U.S. Pub. No. 2011/0087213, entitled "Surgical Generator for Ultrasonic and Electrosurgical Devices," published Apr. 14, 2011, now U.S. Pat. No. 8,951,248, issued Feb. 10, 2105, the disclosure of which is incorporated by reference herein; U.S. Pub. No. 2011/0087214, entitled "Surgical Generator for Ultrasonic and Electrosurgical Devices," published Apr. 14, 2011, now U.S. Pat. No. 9,039,695, issued May 26, 2015, the disclosure of which is incorporated by reference herein; U.S. Pub. No. 2011/0087215, entitled "Surgical Generator for Ultrasonic and Electrosurgical Devices," published Apr. 14, 2011, now U.S. Pat. No. 9,050,093, issued Jun. 9, 2015, the disclosure of which is incorporated by reference herein; U.S. Pub. No. 2011/0087216, entitled "Surgical Generator for Ultrasonic and Electrosurgical Devices," published Apr. 14, 2011, now U.S. Pat. No. 8,956,349, issued Feb. 17, 2015, the disclosure of which is incorporated by reference herein; and/or U.S. Pub. No. 2011/0087217, entitled "Surgical Generator for Ultrasonic and Electrosurgical Devices," published Apr. 14, 2011, now U.S. Pat. No. 9,060,776, issued Jun. 23, 2015, the disclosure of which is incorporated by reference herein. Other suitable configurations for power source (80) and controller (82) will be apparent to those of ordinary skill in the art in view of the teachings herein.

As best seen in FIG. 4, the lower side of first jaw (42) includes a longitudinally extending recess (58) adjacent to slot (46); while the upper side of second jaw (44) includes a longitudinally extending recess (59) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. In other words, it should be understood that serrations may be generally blunt or otherwise atraumatic. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44). In some versions, serrations (46, 48) are electrically conductive.

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56) at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. In some versions, a proximal end of firing beam (60) is secured to a firing tube or other structure within shaft (30); and the firing tube or other structure extends through the remainder of shaft (30) to handpiece (20) where it is driven by movement of trigger (24). Firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode.

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze trigger (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (44) when firing beam (60) is retracted to a proximal position and to hold jaw (44) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

Figure 5:
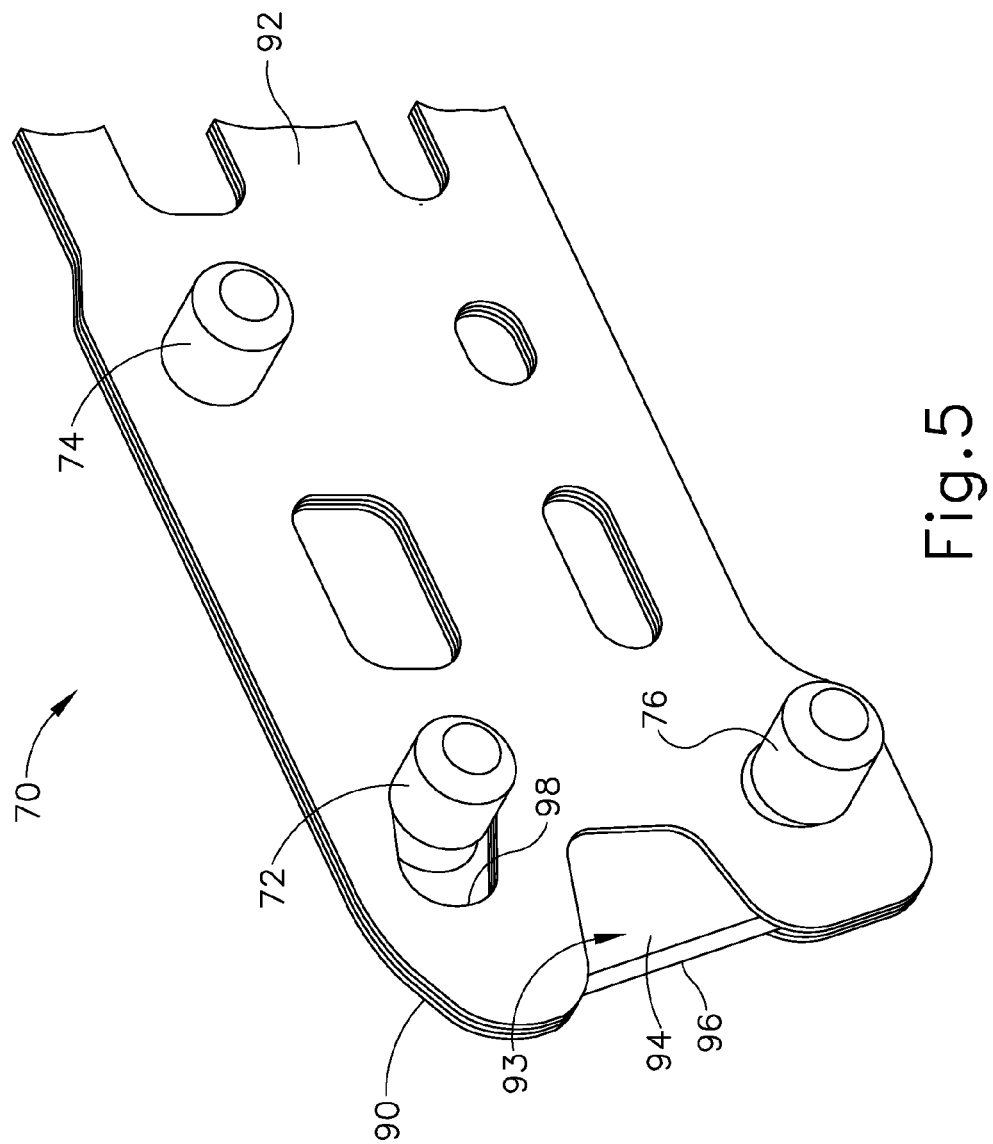
FIG. 5 depicts a partial perspective view of the distal end of an exemplary alternative firing beam suitable for incorporation in the instrument of FIG. 1.

FIG. 5 shows an exemplary alternative firing beam (70), which may be readily substituted for firing beam (60). In this example, firing beam (70) comprises a blade insert (94) that is interposed between two beam plates (90, 92). Blade insert (94) includes a sharp distal edge (96), such that blade insert (94) will readily sever tissue that is captured between jaws (42, 44). Sharp distal edge (96) is exposed by a proximally extending recess (93) formed in plates (90, 92). A set of pins (72, 74, 76) are transversely disposed in plates (90, 92). Pins (72, 74) together effectively serve as substitutes for upper flange (62); while pin (76) effectively serves as a substitute for lower flange (66). Thus, pins (72, 74) bear against channel (59) of jaw (44), and pin (76) bears against channel (58) of jaw (42), as firing beam (70) is translated distally through slots (46, 48). Pins (72, 74, 76) of the present example are further configured to rotate within plates (90, 92), about the axes respectively defined by pins (72, 74, 76). It should be understood that such rotatability of pins (72, 74, 76) may provide reduced friction with jaws (42, 44), thereby reducing the force required to translate firing beam (70) distally and proximally in jaws (42, 44). Pin (72) is disposed in an angled elongate slot (98) formed through plates (90, 92), such that pin (72) is translatable along slot (98). In particular, pin (72) is disposed in the proximal portion of slot (98) as firing beam (70) is being translated distally. When firing beam (70) is translated proximally, pin (72) slides distally and upwardly in slot (98), increasing the vertical separation between pins (72, 76), which in turn reduces the compressive forces applied by jaws (42, 44) and thereby reduces the force required to retract firing beam (70). Pins (72, 74, 76) may be pinged, upended, or otherwise configured to provide further retention in the body of firing beam (70). Of course, firing beam (70) may have any other suitable configuration. By way of example only, firing beam (70) may be configured in accordance with at least some of the teachings of U.S. Pub. No. 2012/0083783, now U.S. Pat. No. 8,888,809, the disclosure of which is incorporated by reference herein.

D. Exemplary Operation

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (42) toward jaw (44) when firing beam (60) is actuated distally by squeezing trigger (24) toward pistol grip (22). Jaws (42, 44) may be substantially clamping tissue before trigger (24) has swept through a full range of motion toward pistol grip (22), such that trigger (24) may continue pivoting toward pistol grip (22) through a subsequent range of motion after jaws (42, 44) have substantially clamped on the tissue.

With tissue layers captured between jaws (42, 44) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, help keep jaws (42, 44) in a closed and tightly clamping position. In particular, flanges (62, 66) help maintain a significantly compressive force between jaws (42, 44). With severed tissue layer portions being compressed between jaws (42, 44), bipolar RF energy is applied to the tissue through electrode surfaces (50, 52) by the user depressing activation button (26). Thus, a bipolar RF current flows through the compressed regions of severed tissue layer portions. The bipolar RF energy delivered by power source (80) ultimately thermally welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52). Other suitable ways in which instrument (10) may be operable and operated will be apparent to those of ordinary skill in the art in view of the teachings herein.

II. Exemplary Split Jaw End Effector Assembly

In some instances, it may be desirable to use jaws (42, 44) for blunt tissue dissection, otomy creation, otomy expansion, and/or other operations. This may be performed by placing jaws (42, 44) in between tissue or two anatomical structures, or within an incision, while jaws (42, 44) are in a closed position. Jaws (42, 44) may then be opened to spread apart or bluntly dissect the tissue. Jaws (42, 44) may open in one plane to dissect tissue and then close to efficiently grasp tissue between jaws (42, 44). In some instances, it may be desirable to provide a jaw (42, 44) that spreads open to two or more planes to widen the dissection and to increase visibility for the user. Accordingly, an end effector (40) may be provided with jaws (42, 44) that close in one plane for grasping tissue and then spread open to two or more planes for dissecting tissue. The examples below include several merely illustrative versions of jaw spreading features that may be readily introduced to an instrument (10).

A. Exemplary End Effector

Figure 6:
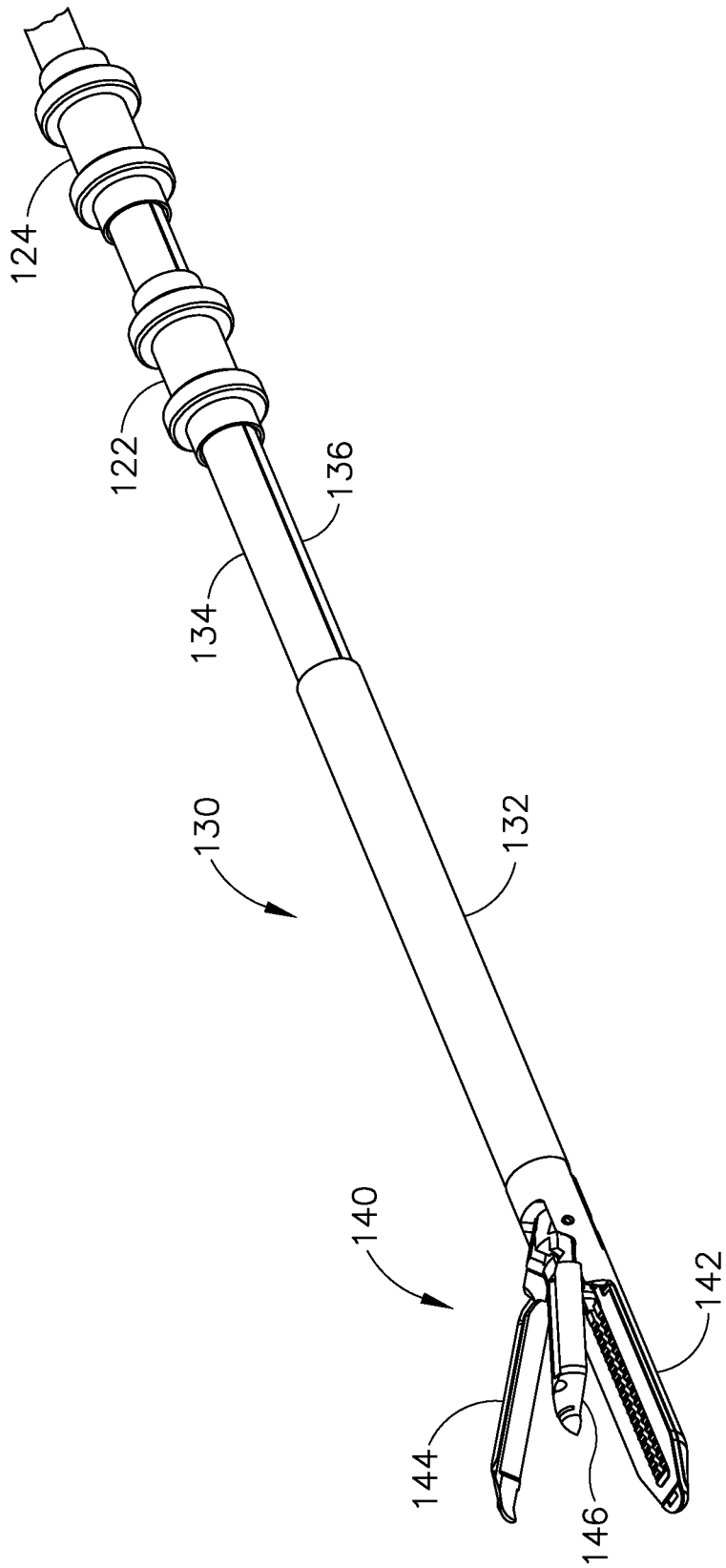
FIG. 6 depicts a perspective view of another exemplary end effector and shaft assembly suitable for incorporation in the instrument of FIG. 1.
Figure 7:
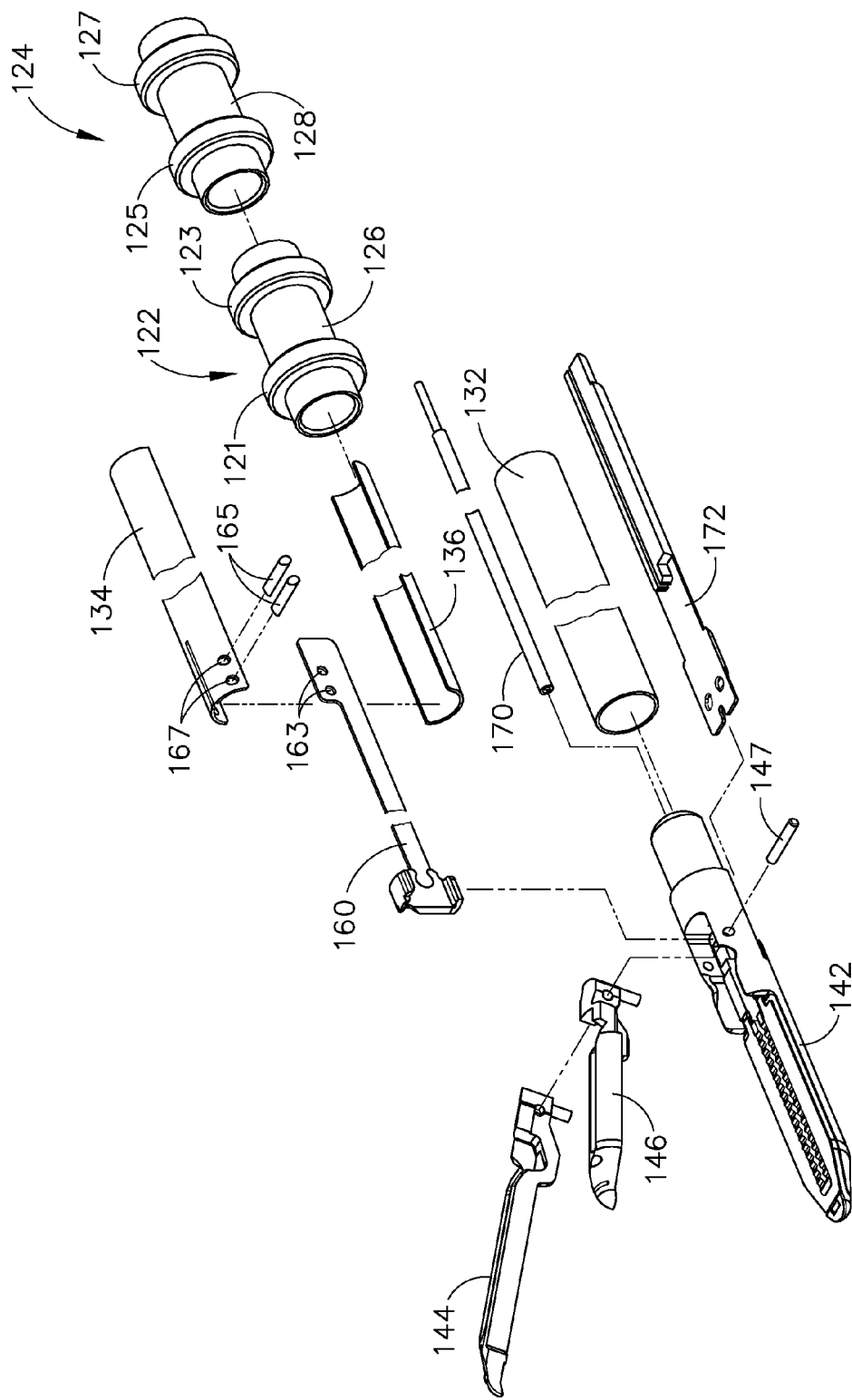
FIG. 7 depicts an exploded view of the end effector and shaft assembly of FIG. 6.
Figure 8:
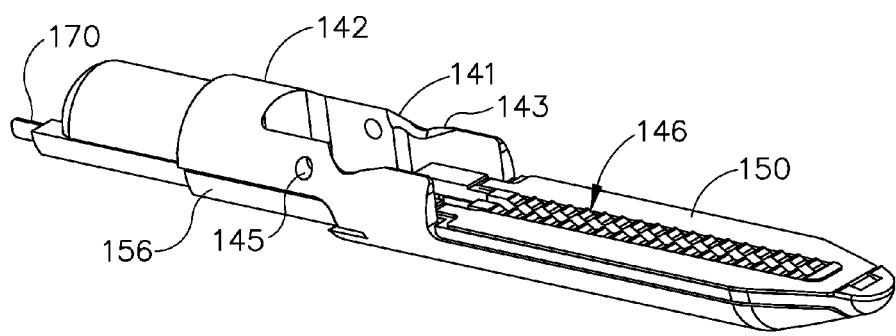
FIG. 8 depicts a perspective view of a lower jaw of the end effector of FIG. 6.
Figure 9:
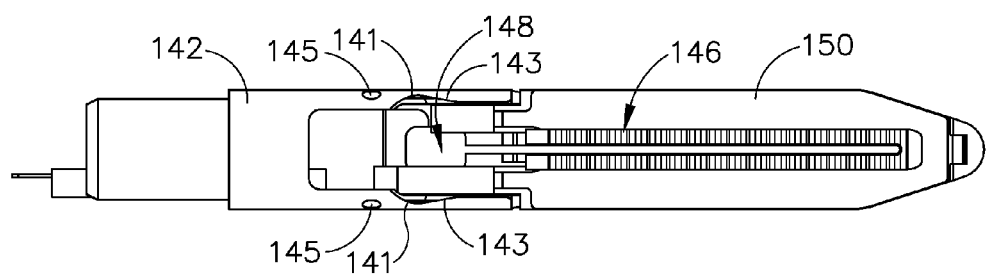
FIG. 9 depicts a top plan view of the lower jaw of FIG. 8.

FIGS. 6-7 show an exemplary end effector (140) that is similar to end effector (40), except that end effector (140) comprises a pair of upper jaws (144, 146) that are configured to spread apart when opened. End effector (140) comprises a lower jaw (142), upper jaws (144, 146), slider (172), and firing beam (160). As best seen in FIGS. 8-9, lower jaw (142) is similar to lower jaw (42), except that lower jaw (142) comprises ramped surfaces (141, 143). Ramped surfaces (141, 143) are positioned on each side of a proximal portion of lower jaw (142). Each ramped surface (141, 143) slopes inwardly to guide upper jaws (144, 146) to a closed position when upper jaws (144, 146) are pivoted toward lower jaw (142). Lower jaw (142) further defines a recess (148) that is configured to receive a portion of upper jaws (144, 146) when upper jaws (144, 146) are in a closed position. Recess (148) is in communication with the proximal end of channel (146) of lower jaw (142). In the present example, an electrode conductor (156) is routed along an exterior surface of lower jaw (142) to connect electrode surface (150) with a power source (80) via cable (170).

Figure 10:
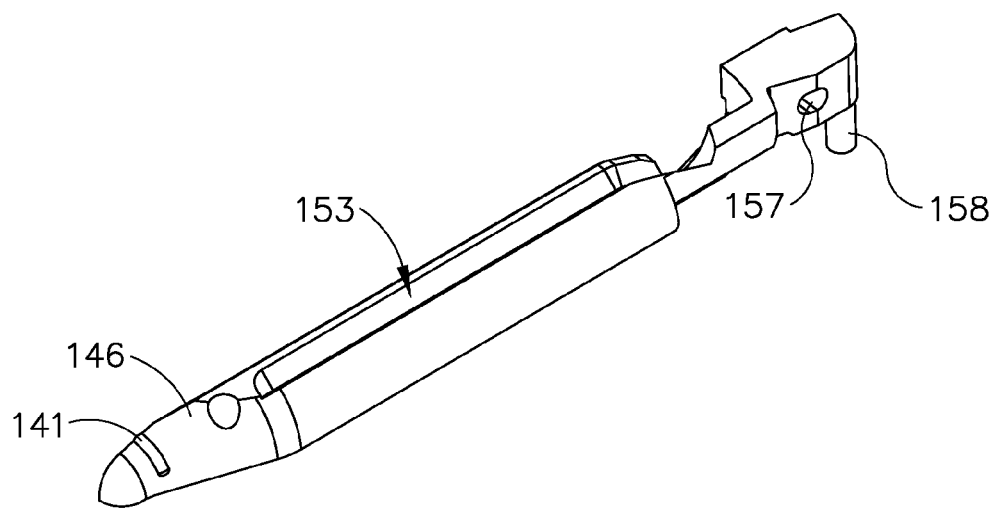
FIG. 10 depicts a perspective view of an upper jaw half of the end effector of FIG. 6.
Figure 11:
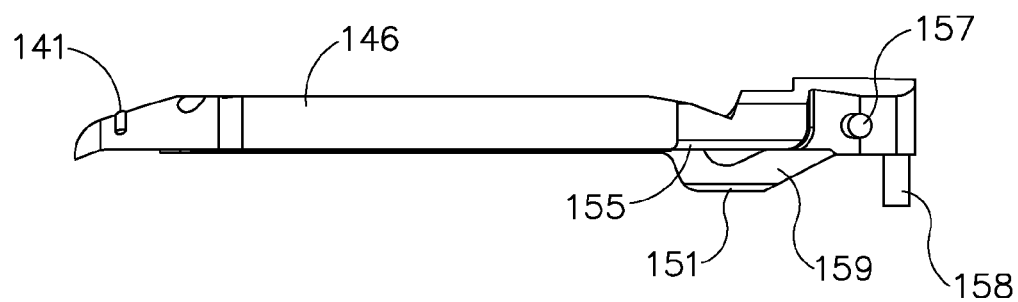
FIG. 11 depicts a side elevational view of the upper jaw half of FIG. 10.
Figure 12:
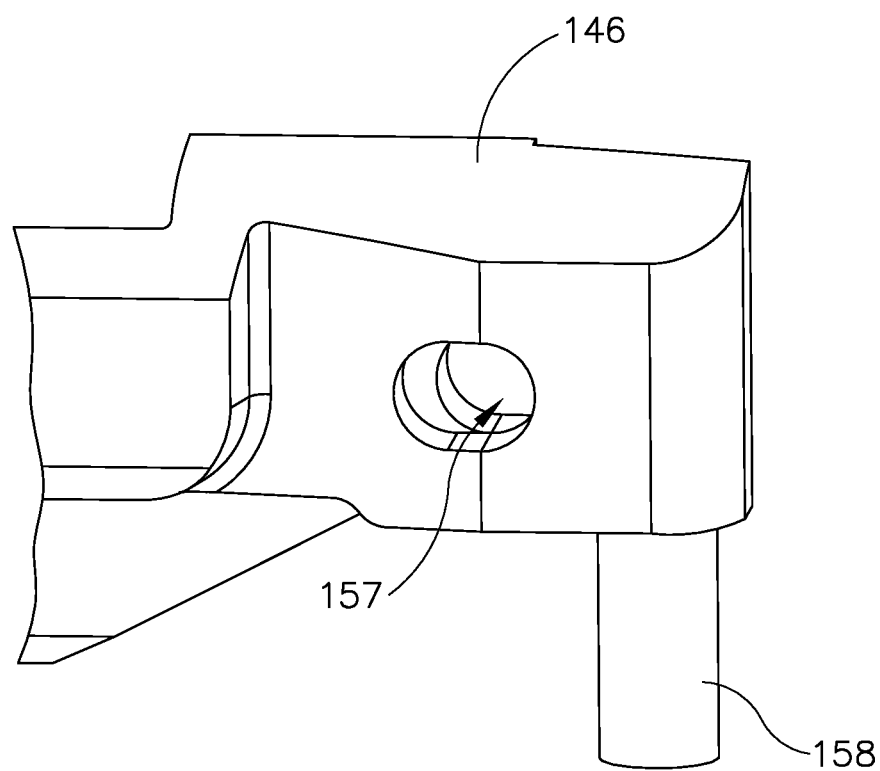
FIG. 12 depicts a partial perspective view of the upper jaw half of FIG. 10.

A pair of upper jaws (144, 146) are coupled with lower jaw (142). While FIGS. 10-12 show a single upper jaw (146), it should be noted that upper jaw (144) is a mirror image of upper jaw (146). An outer proximal portion of upper jaw (146) includes a ramped surface (155) extending inwardly from upper jaw (146). Ramped surface (155) is configured to correspond to ramped surfaces (141, 143) of lower jaw (142) such that ramped surface (155) cammingly engages ramped surfaces (141, 143) to guide upper jaw (146) within lower jaw (142) when upper (146) is closed relative to lower jaw (142). Upper jaw (146) further comprises a fin (159) extending downwardly from a proximal portion of upper jaw (146), as shown in FIG. 11. Fin (159) includes a ramped surface (151) sloping inwardly on upper jaw (146). Fin (159) is configured to be inserted within recess (148) of lower jaw (142). Ramped surface (151) of fin (159) cammingly engages lower jaw (142) as upper jaw (146) is closed relative to lower jaw (142) to guide fin (159) within recess (148). As upper jaw (146) opens relative to lower jaw (142), fin (159) remains within recess (148) to restrict lateral movement of upper jaw (146) relative to lower jaw (142). Upper jaw (146) then continues to pivot away from lower jaw (142) such that fin (159) exits recess (148) to allow upper jaw (146) to pivot outwardly and away from lower jaw (142). For instance, upper jaw (146) may pivot about 18 to about 20 degrees away from lower jaw (142) with fin (159) positioned within recess (148) such that upper jaw (146) is laterally aligned with lower jaw (142). Fin (159) may then exit recess (148) to allow upper jaw (146) to pivot outwardly as upper jaw (146) pivots further to about 25 degrees away from lower jaw (142). Of course, any other suitable angles may be used.

Upper jaw (146) further defines an opening (157) at the proximal portion of upper jaw (146). Opening (157) corresponds to opening (145) on lower jaw (142) such that a pin (147) may be inserted within openings (157, 145) to allow upper jaw (146) to pivot relative to lower jaw (142). As best seen in FIG. 12, opening (157) comprises a pair of misaligned slots to allow upper jaw (146) to only rotate along two planes relative to lower jaw (142). The proximal portion of upper jaw (146) also comprises a protrusion (158) extending downwardly from upper jaw (146). Protrusion (158) is coupled with slider (172). A channel (153) extends longitudinally along an exterior surface of upper jaw (146) to receive firing beam (160), as shown in FIG. 10. A tip feature (141) protrudes transversely across the distal portion of upper jaw (146). Tip feature (141) may aid in gripping tissue during blunt dissection of the tissue, or may otherwise aid in performing blunt dissections using upper jaw (146).

Figure 13:
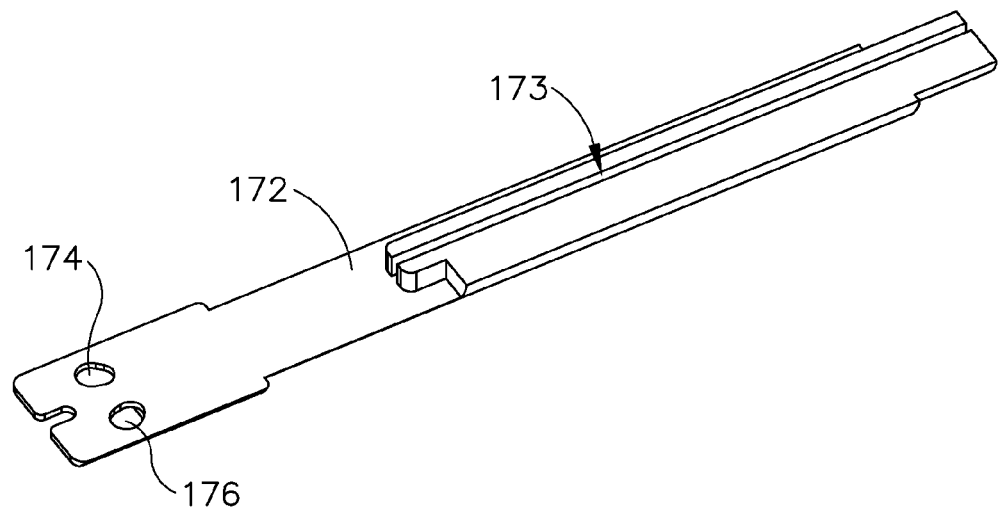
FIG. 13 depicts a perspective view of a slider of the end effector of FIG. 6.
Figure 14:
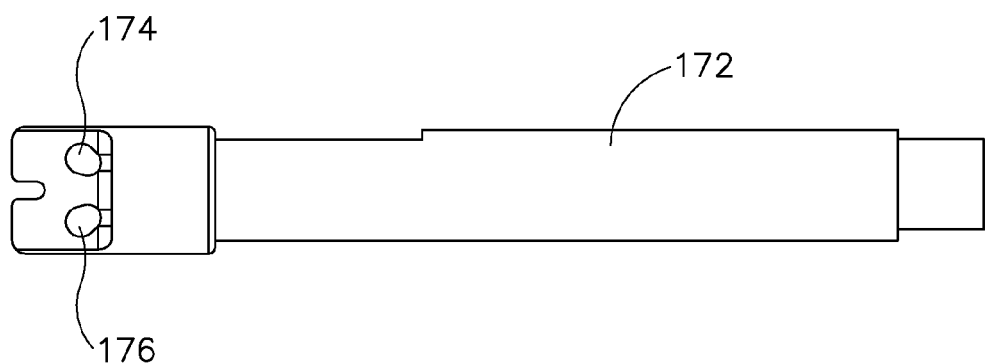
FIG. 14 depicts a bottom view of the slider of FIG. 13.
Figure 15:
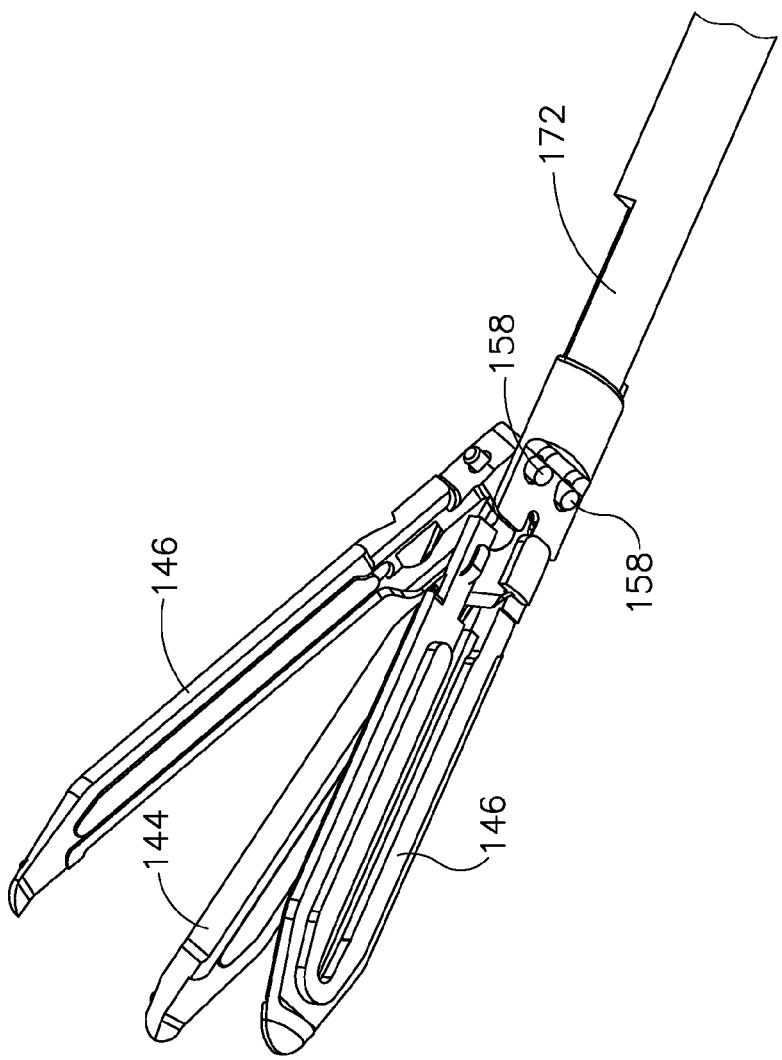
FIG. 15 depicts a bottom perspective view of the end effector of FIG. 6.

FIGS. 13-14 show slider (172) defining openings (174, 176) on the distal portion of slider (172). Openings (174, 176) are positioned to angle outwardly along slider (172), as shown in FIG. 14. Opening (174) is configured to receive protrusion (158) of upper jaw (144) and opening (176) is configured to receive protrusion (158) of upper jaw (146), as shown in FIG. 15. In the present example, slider (172) is positioned proximal to lower jaw (142) within outer sheath (132) and slider (172) is configured to translate relative to lower jaw (142). Accordingly, when slider (172) is translated distally, openings (174, 176) cammingly engage protrusions (158) of upper jaws (144, 146) to pivot upper jaws (144, 146) away from each other. When slider (172) is translated proximally, openings (174, 176) cammingly engage protrusions (158) of upper jaws (144, 146) to pivot upper jaws (144, 146) toward each other. Slider (172) also defines a channel (173) on a top surface of slider (172) to receive the bottom portion of firing beam (160).

Figure 17:
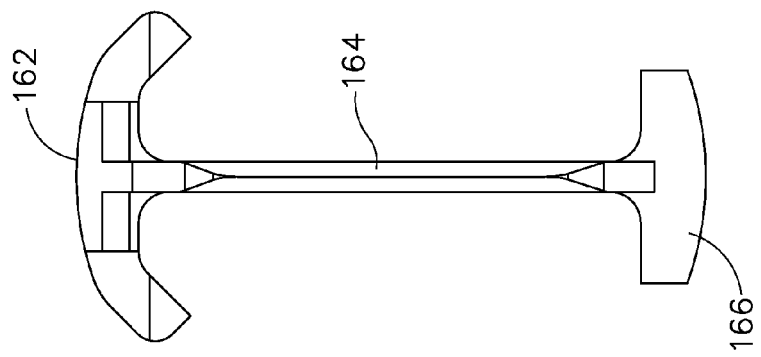
FIG. 17 depicts a front view of the firing beam of FIG. 16.
Figure 16:
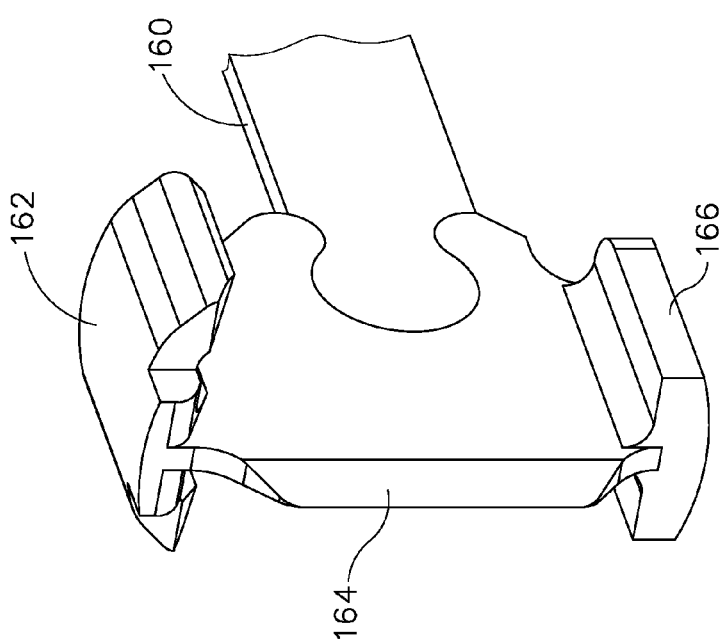
FIG. 16 depicts a partial perspective view of a firing beam of the end effector of FIG. 6.
Figure 18:
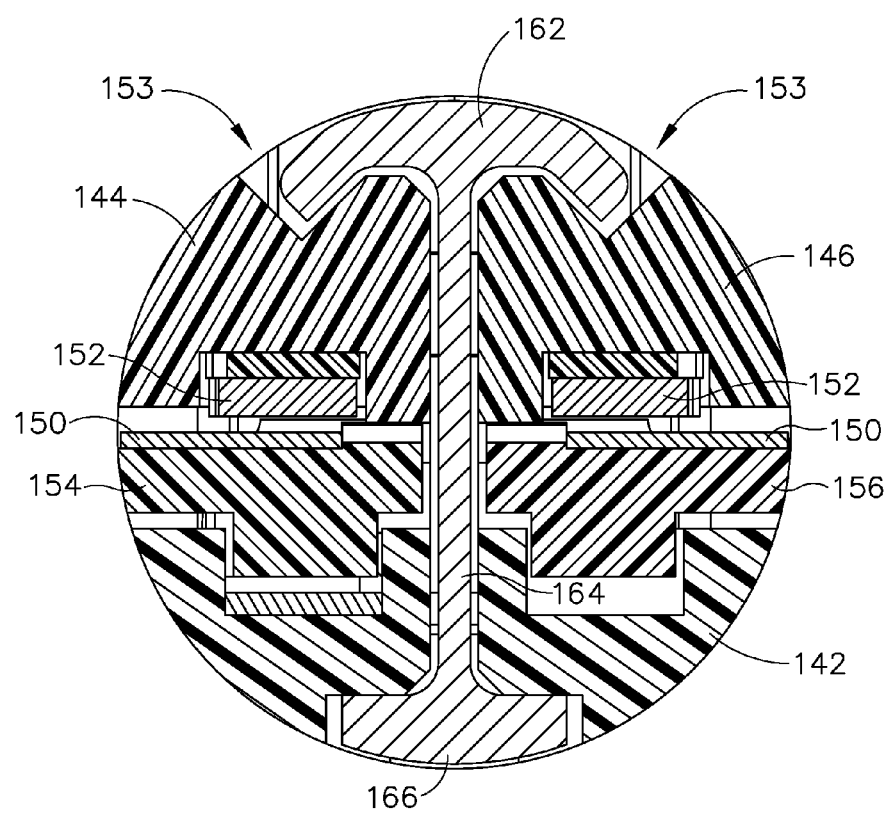
FIG. 18 depicts a cross-sectional view of the firing beam of FIG. 16 within the end effector.

FIGS. 16-17 show firing beam (160), which is similar to firing beam (60), except that firing beam (160) comprises a curved upper flange (162). As best seen in FIG. 17, upper flange (162) of firing beam (160) curves downwardly as upper flange (162) extends from firing beam (160). Each side of upper flange (162) is positioned within a respective channel (153) of upper jaws (144, 146), as shown in FIG. 18. Upper flange (162) thereby engages upper jaws (144, 146) to further maintain the lateral position of upper jaws (144, 146) when firing beam (160) is advanced within end effector (140). FIG. 18 also shows that the top side of lower jaw (142) presents a first electrode surface (150); while the underside of upper jaws (144, 146) presents a second electrode surface (152). Electrode surfaces (150, 152) are in communication with an electrical source (80) via one or more conductors (170) that extend along the length of shaft (130). These conductors (170) are coupled with electrical source (80) and a controller (82) via a cable (84), which extends proximally from handpiece (20). Electrical source (80) is operable to deliver RF energy to first electrode surface (150) and to second electrode surface (152), such that RF current flows between electrode surfaces (150, 152) and thereby through tissue captured between jaws (142, 144, 146). In some versions, firing beam (160) serves as an electrical conductor that cooperates with electrode surfaces (150, 152) (e.g., as a ground return) for delivery of bipolar RF energy captured between jaws (142, 144, 146). Alternatively, firing beam (160) may be used as an electrode in addition to or in lieu of electrode surfaces (152). It should also be understood that electrode surfaces (150, 152) may be provided in a variety of alternative locations, configurations, and relationships B. Exemplary Shaft Assembly Shaft assembly (130) is similar to shaft assembly (30), except that shaft assembly (130) comprises actuators (122, 124). In some versions, shaft assembly (130) is rotatable about its longitudinal axis, relative to handpiece (120), via a knob (138). Knob (138) may be substantially similar to knob (34) referenced above. As shown in FIG. 7, a first actuator (122) comprises a tubular member (126) positioned between a pair of annular flanges (121, 123). First actuator (122) is positioned around and secured to a first translating member (134) housed within outer sheath (132). The distal end of first translating member (134) includes one or more openings (167) that couple with one or more openings (163) on the proximal end of firing beam (160) via pins (165). Accordingly, when first actuator (122) is translated distally, first actuator (122) translates first translating member (134) and firing beam (160) distally to advance firing beam (160) within end effector (140). When first actuator (122) is translated proximally, first actuator (122) translates first translating member (134) and firing beam (160) proximally to retract firing beam (160). It should be noted that first translating member (134) is merely optional, such that first actuator (122) may be directly coupled with firing beam (160).

A second actuator (124) comprises a tubular member (128) positioned between a pair of annular flanges (125, 127). Second actuator (124) is positioned around and secured to a second translating member (136) housed within outer sheath (132). The distal end of second translating member (136) is coupled with the proximal end of slider (172). Accordingly, when second actuator (124) is translated distally, second actuator (124) translates second translating member (136) and slider (172) distally to pivot upper jaws (144, 146) away from lower jaw (142) and away from each other. When second actuator (124) is translated proximally, second actuator (124) translates second translating member (136) and slider (172) proximally to pivot upper jaws (144, 146) toward lower jaw (142) and toward each other. It should be noted that second translating member (136) is merely optional, such that second actuator (124) may be directly coupled with slider (172).

Figure 23A:
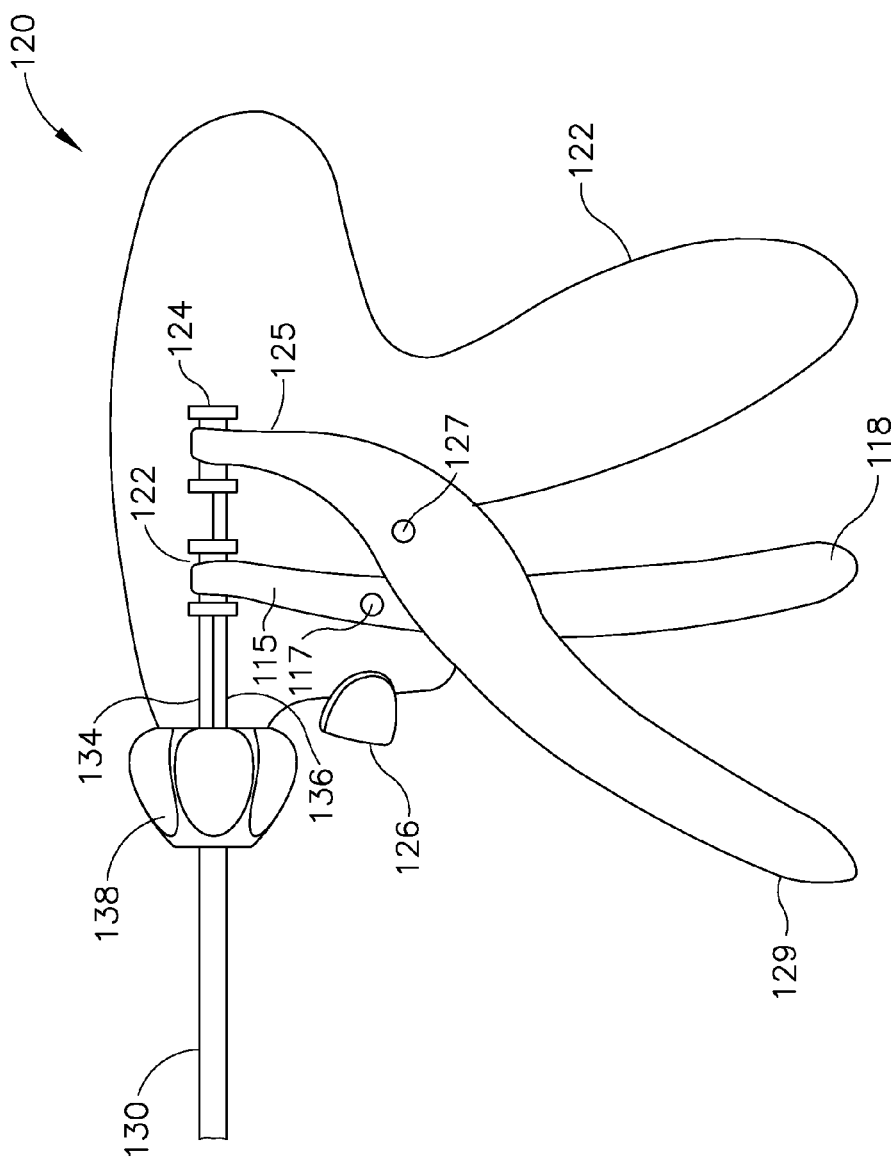
FIG. 23A depicts a cross-sectional view of an exemplary handpiece for use with the end effector of FIG. 6, with a first and second trigger in an initial position.
Figure 23B:
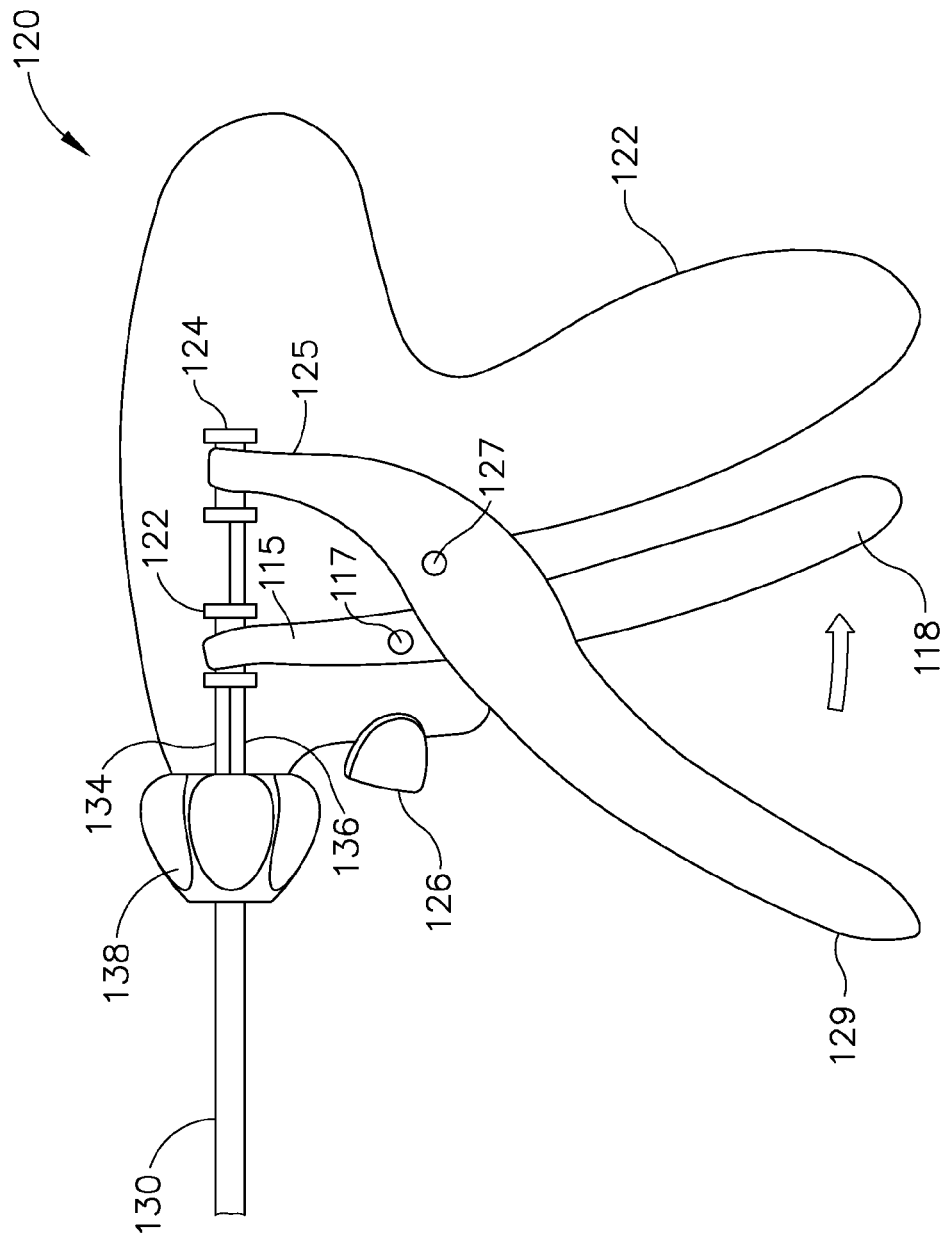
FIG. 23B depicts a cross-sectional view of the handpiece of FIG. 23A, with the first trigger in a fired position and the second trigger in the initial position.
Figure 23C:
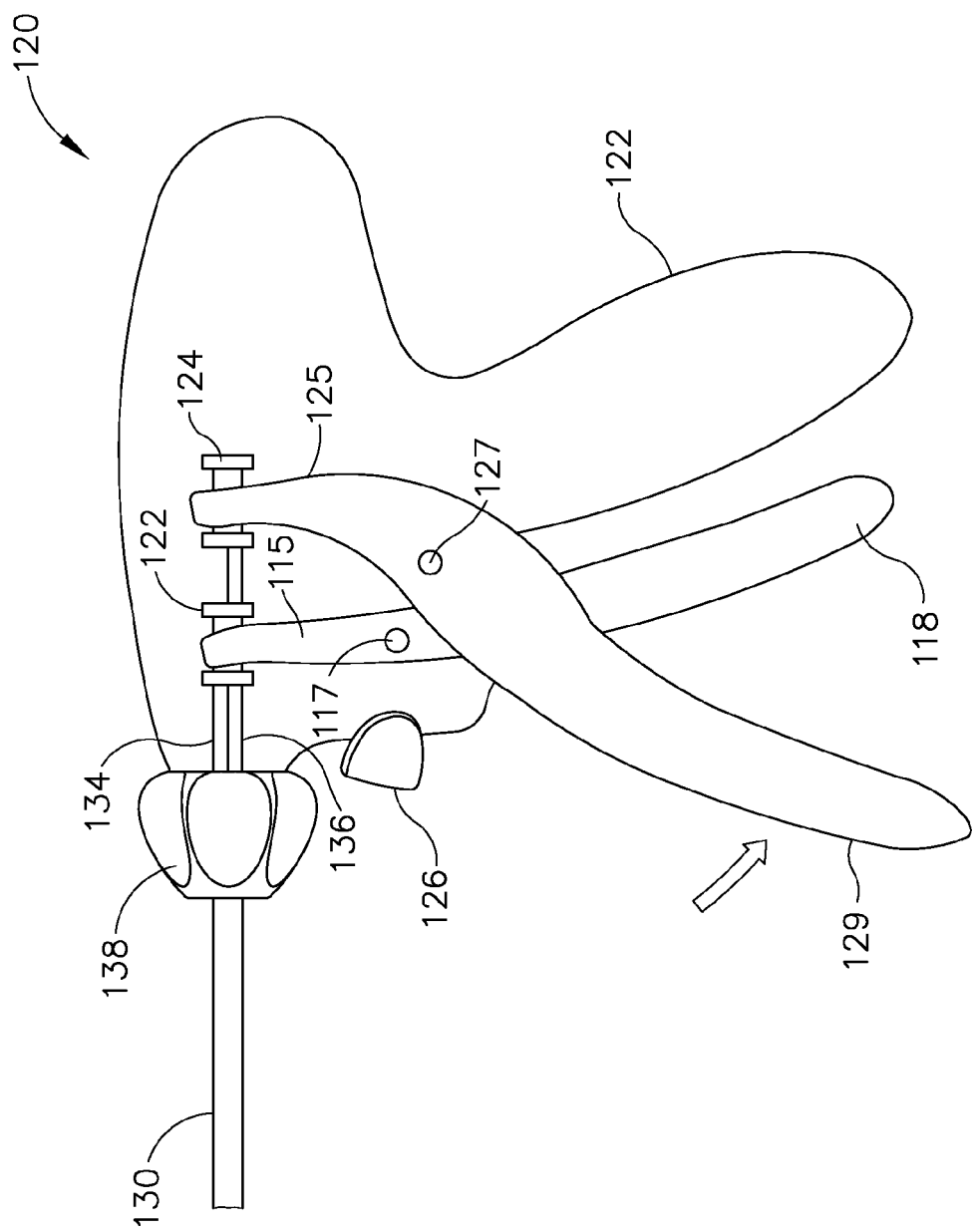
FIG. 23C depicts a cross-sectional view of the handpiece of FIG. 23A, with the first trigger in the initial position and the second trigger in a first fired position.
Figure 23D:
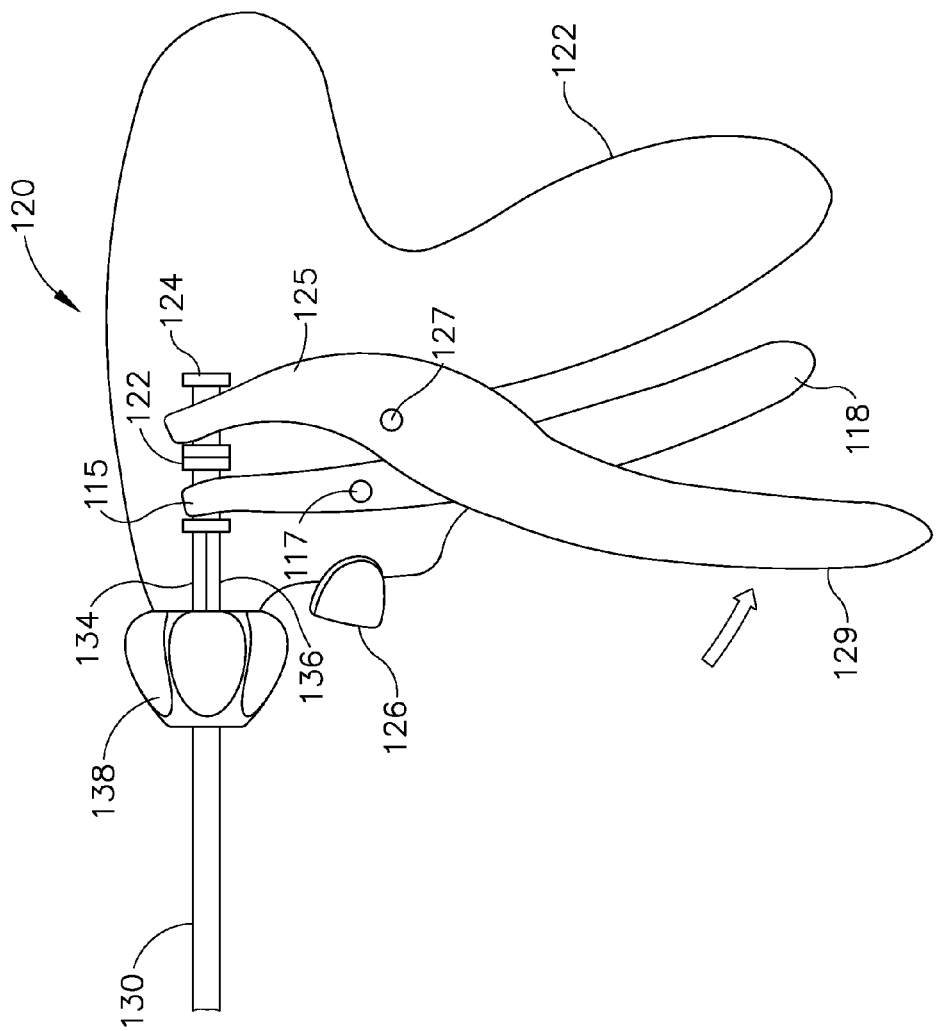
FIG. 23D depicts a cross-sectional view of the handpiece of FIG. 23A, with the first trigger in the initial position and the second trigger in a second fired position.

Actuators (122, 124) may be coupled to and driven by a handpiece assembly (120), as shown in FIGS. 23A-23D. Handpiece assembly (120) is similar to handpiece assembly (20) described above, except that handpiece assembly (120) comprises a first trigger (118) and a second trigger (129). First trigger (118) comprises an extension (115) that is coupled with first actuator (122). First trigger (118) is pivotable relative to handpiece (120) via pin (117). Second trigger (129) comprises an extension (125) that is coupled with second actuator (124). Second trigger (129) is pivotable relative to handpiece (120) via pin (127). As shown in FIG. 23A, first and second triggers (118, 124) are in an initial position such that upper jaws (144, 146) are in a closed position. As shown in FIG. 23B, first trigger (118) is pivoted toward grip (122) such that extension (115) of first trigger (118) translates first actuator (122) distally. As described above, first actuator (122) thereby translates firing beam (160) distally. As shown in FIG. 23C, first trigger (118) is returned to the initial position, and second trigger (129) is pivoted toward grip (122) such that extension (125) of second trigger (129) translates second actuator (124) distally to a first position. In this first position, second actuator (124) translates second translating member (136) and slider (172) to a first distal position such that upper jaws (144, 146) pivot away from lower jaw (142) along a vertical plane. As shown in FIG. 23D, second trigger (129) is pivoted further toward grip (122) such that extension (125) translates second actuator (124) further distally to a second position. In this second position, second actuator (124) translates second translating member (126) and slider (172) to a second distal position such that upper jaws (144, 146) pivot further away from lower jaw (142) and pivot away from each other.

In some instances, handpiece (120) may comprise an indicator to indicate to a user when second trigger (129) transitions from the first distal position to the second distal position when upper jaws (144, 146) are pivoted away from each other. For instance, second trigger (129) may pivot past an indicator (e.g., a detent, a switch, etc.) positioned within handpiece (124) to provide audio, visual, and/or tactile feedback to the user when upper jaws (144, 146) begin to pivot away from each other. Second trigger (129) may also engage a spring or other resilient member when second trigger (129) transitions from the first distal position to the second distal position. This may change the force required to pivot second trigger (129), thereby providing tactile feedback to alert the user that upper jaws (144, 146) are pivoting away from each other. Alternatively, second trigger (129) may be pivoted in a first direction to spread upper jaws (144, 146) away from each other and in a second direction to close upper jaws (144, 146) relative to lower jaw (142). For instance, upper jaws (144, 146) may be positioned in an open position when second trigger (129) is in the initial position shown in FIG. 23A. Second trigger (129) may then be pivoted away from grip (122) to translate second actuator (124) and slider (172) distally to further open upper jaws (144, 146) and to spread jaws (144, 146) away from each other. Second trigger (129) may be pivoted from the initial position toward grip (122) to translate second actuator (124) and slider (172) proximally to close upper jaws (144, 146) relative to lower jaw (142). Various suitable components that may be coupled between second trigger (129) and second actuator (124) to provide such functionality will be apparent to those of ordinary skill in the art in view of the teachings herein.

Figure 24A:
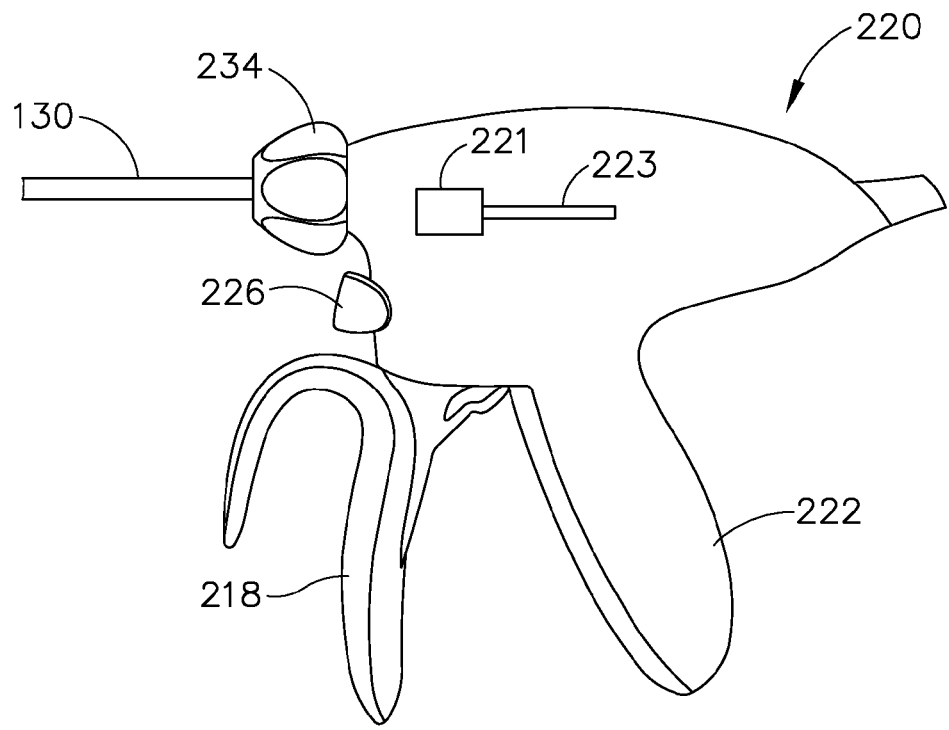
FIG. 24A depicts a side elevational view of another exemplary handpiece for use with the end effector of FIG. 6, in a first position.
Figure 24B:
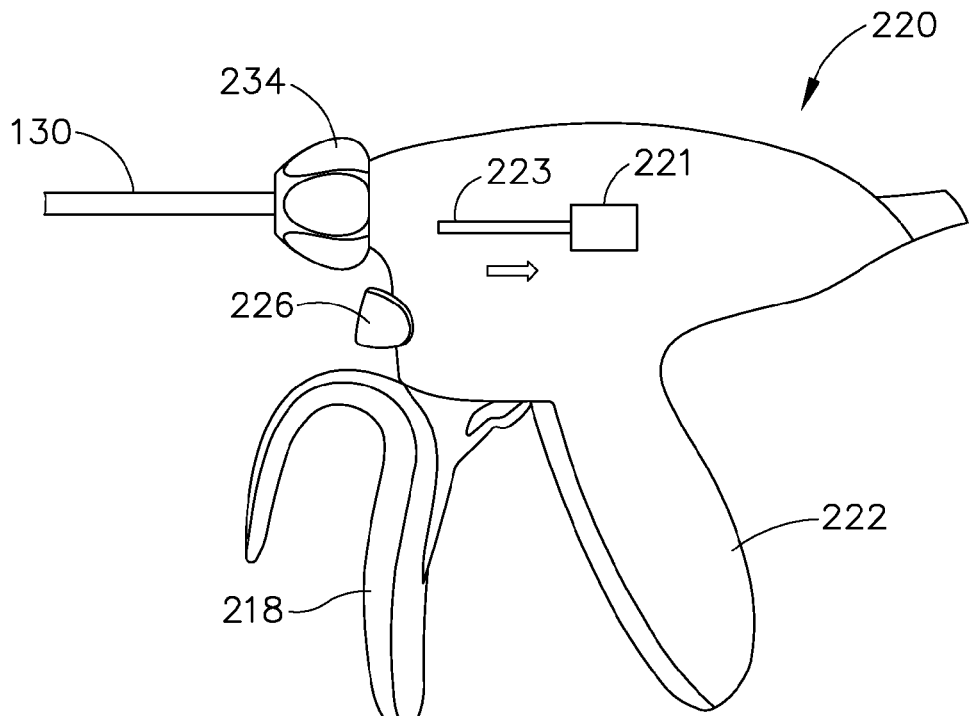
FIG. 24B depicts a side elevational view of the handpiece of FIG. 24A, in a second position.

In some instances, handpiece (120) may comprise a single pivoting trigger. For instance, FIGS. 24A-24B show another exemplary handpiece (220) that is similar to handpiece (120), except that handpiece (220) comprises a slider (221) instead of second trigger (224). Slider (221) is positioned on an exterior surface of handpiece (220) and extends through slot (223) of handpiece (220) to couple with second actuator (224). Accordingly, slider (221) is translated relative to handpiece (220) to actuate second actuator (224) and upper jaws (144, 146). As shown in FIG. 24A, slider (221) is in a distal position such that upper jaws (144, 146) are pivoted away from lower jaw (142) and away from each other. Slider (221) is translated to a proximal position within slot (223) of handpiece (220), shown in FIG. 24B, to translate second actuator (124) and slider (172) proximally to pivot upper jaws (144, 146) toward lower jaw (142) and toward each other. Handpiece (220) may also include an indicator (e.g., a detent, switch, etc.) to indicate to a user when slider (221) is translated to drive second actuator (124) to pivot upper jaws (144, 146) away from each other. Alternatively, second actuator (124) may be driven by the same trigger (218) that drives first actuator (122). Other suitable methods to drive first and second actuators (122, 124) will be apparent to one with ordinary skill in the art in view of the teachings herein.

C. Exemplary Operation

Figure 19A:
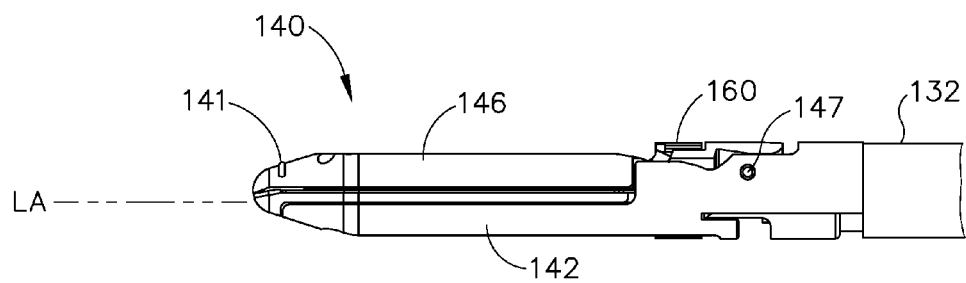
FIG. 19A depicts a side elevational view of the end effector of FIG. 6 in a closed position.
Figure 19B:
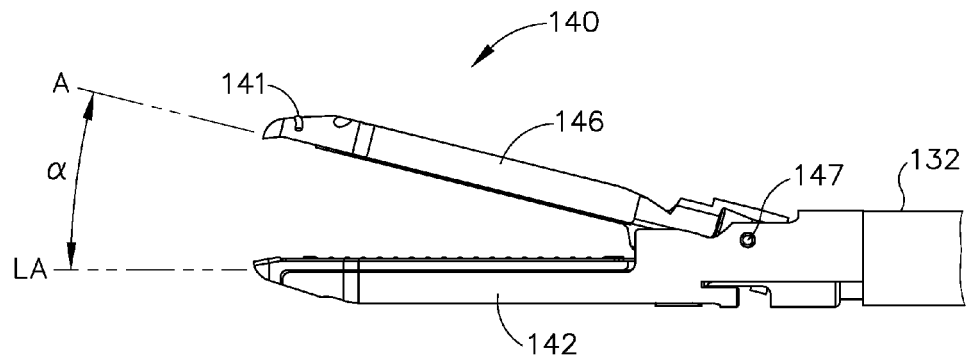
FIG. 19B depicts a side elevational view of the end effector of FIG. 6 in a first open position.
Figure 20A:
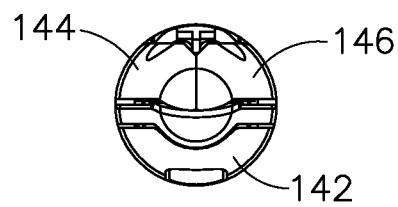
FIG. 20A depicts a front view of the end effector of FIG. 6 in the closed position.
Figure 20B:
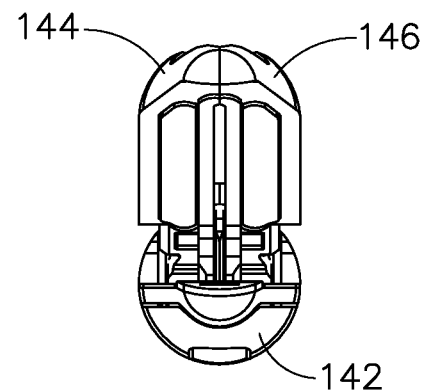
FIG. 20B depicts a front view of the end effector of FIG. 6 in the first open position.
Figure 21A:
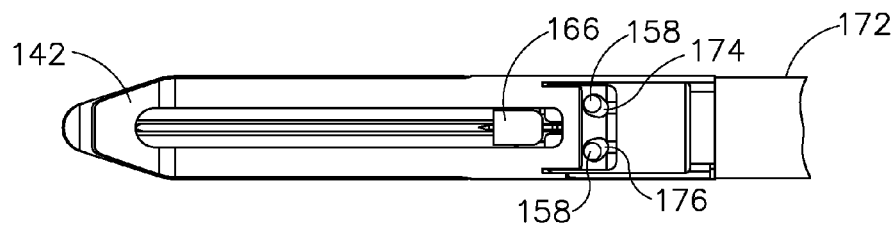
FIG. 21A depicts a bottom view of the end effector of FIG. 6 in the closed position.
Figure 21B:
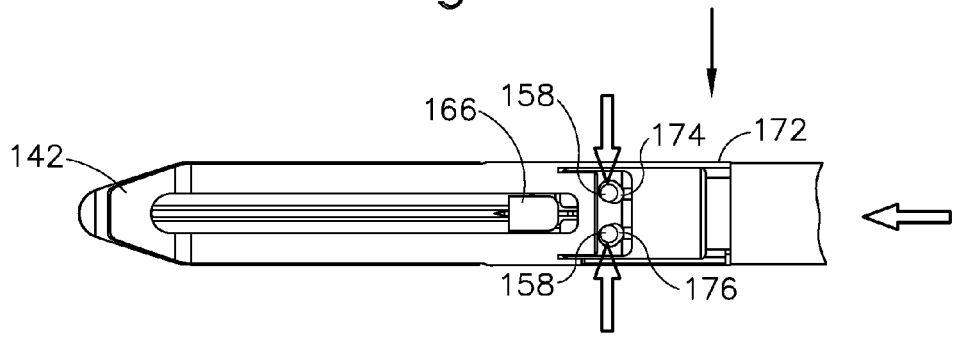
FIG. 21B depicts a bottom view of the end effector of FIG. 6 in the first open position.

In an exemplary use for blunt tissue dissection, actuators (122, 124) may be positioned in a proximal position such that jaws (142, 144, 146) are closed and firing beam (160) is retracted, as shown in FIGS. 19A, 20A, and 21A. End effector (140) may then be inserted into a patient via a trocar. Articulation section (36) is substantially straight when end effector (140) and part of shaft (130) are inserted through the trocar. Articulation control (28) may then be manipulated to pivot or flex articulation section (36) of shaft (130) in order to position end effector (140) at a desired position and orientation relative to an anatomical structure within the patient, such as between tissue. To dissect or spread the tissue, jaws (142, 144, 146) may be opened with jaws (142, 144, 146) positioned between the tissue. Second actuator (124) is translated distally to thereby translate second translating member (136) and slider (172) distally. As slider (172) translates distally, openings (174, 176) engage protrusions (158) of upper jaws (144, 146) to pivot upper jaws (144, 146) away from lower jaw (142) along a vertical plane, as shown in FIG. 21B. Openings (174, 176) are positioned to pivot protrusions (158) of upper jaws (144, 146) inwardly to thereby pivot upper jaws (144, 146) away from each other as upper jaws (144, 146) pivot away from lower jaw (142). However, fins (159) of upper jaws (144, 146) are positioned within recess (148) of lower jaw (142) to restrict lateral movement of upper jaws (144, 146) as upper jaws (144, 146) pivot away from lower jaw (142), as shown in FIGS. 19B, 20B, and 21B. As best seen in FIG. 19B, fins (159) remain within recess (148) until upper jaws (144, 146) are pivoted away from the longitudinal axis (LA) of lower jaw (142) to an angle (a). Angle (a) may be about 18 degrees to about 20 degrees, although any other suitable angles may be used.

Figure 19C:
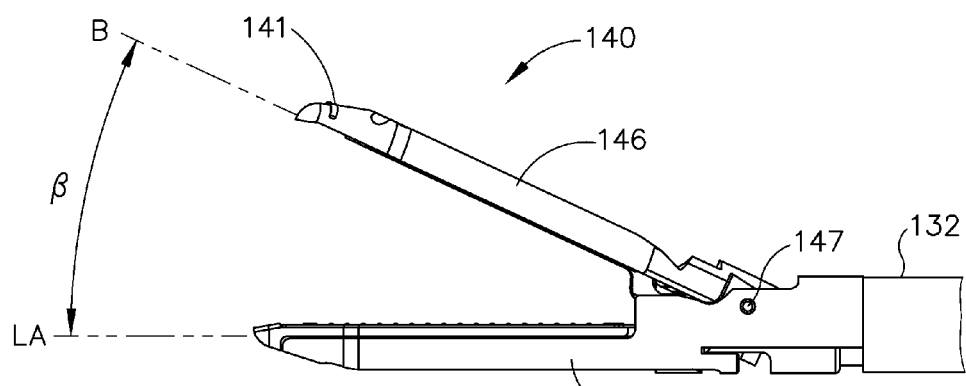
FIG. 19C depicts a side elevational view of the end effector of FIG. 6 in a second open position.
Figure 20C:
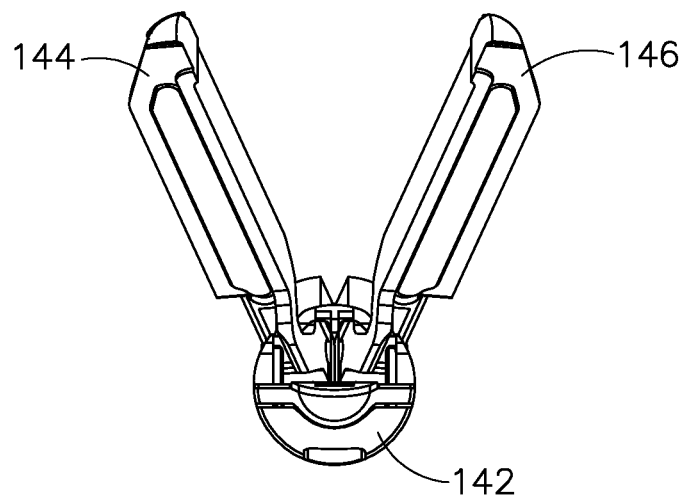
FIG. 20C depicts a front view of the end effector of FIG. 6 in the second open position.
Figure 21C:
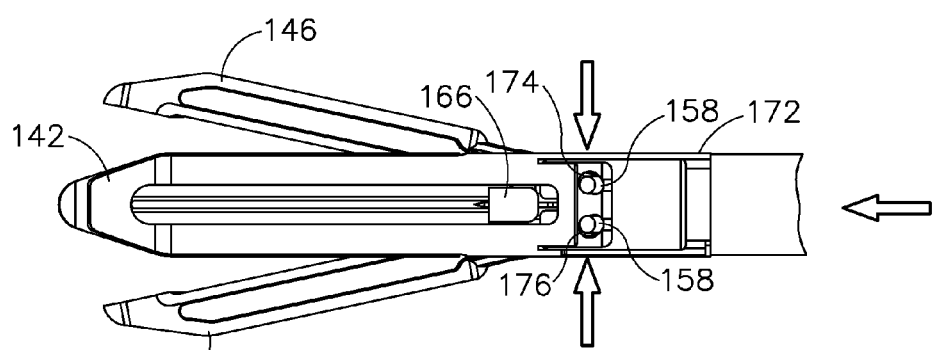
FIG. 21C depicts a bottom view of the end effector of FIG. 6 in the second open position.

As slider (172) continues to translate distally, openings (174, 176) continue to cammingly push upper jaws (144, 146) away from lower jaw (142) and each other, as shown in FIG. 21C. Fins (159) of upper jaws (144, 146) then exit recess (148) of lower jaw (142) to allow upper jaws (144, 146) to pivot outwardly as upper jaws (144, 146) pivot away from lower jaw (142), as shown in FIGS. 19C, 20C, and 21C. As best seen in FIG. 19C, upper jaws (144, 146) are pivoted away from the longitudinal axis (LA) of lower jaw (142) to an angle (β). Angle (β) may be about 25 degrees, although any other suitable angles may be used. Accordingly, upper jaws (144, 146) are pivoted away from lower jaw (142) along a vertical plane and away from each other along respective oblique planes to dissect the tissue.

Second actuator (124) may then be translated proximally to close jaws (142, 144, 146). As second actuator (124) translates proximally, second actuator (124) translates second translating member (126) and slider (172) proximally. Openings (174, 176) of slider thereby pivot upper jaws (144, 146) toward lower jaw (142) and inwardly toward each other, as shown in FIGS. 19B, 20B, and 21B. Ramped surfaces (151) of fins (159) of upper jaws (144, 146) then cammingly engage recess (148) of lower jaw (142) to guide fins (159) within recess (148). Slider (172) continues to translate proximally to pivot upper jaws (144, 146) toward lower jaw (142) to a closed position, as shown in FIGS. 19A, 20A, and 21A. As upper jaws (144, 146) pivot toward lower jaw (142), ramped surfaces (155) of upper jaws (144, 146) cammingly engage ramped surfaces (141, 143) of lower jaw (142) to guide upper jaws (144, 146) to the closed position. Jaws (142, 144, 146) may be again opened and closed to further dissect tissue within the patient.

Figure 22:
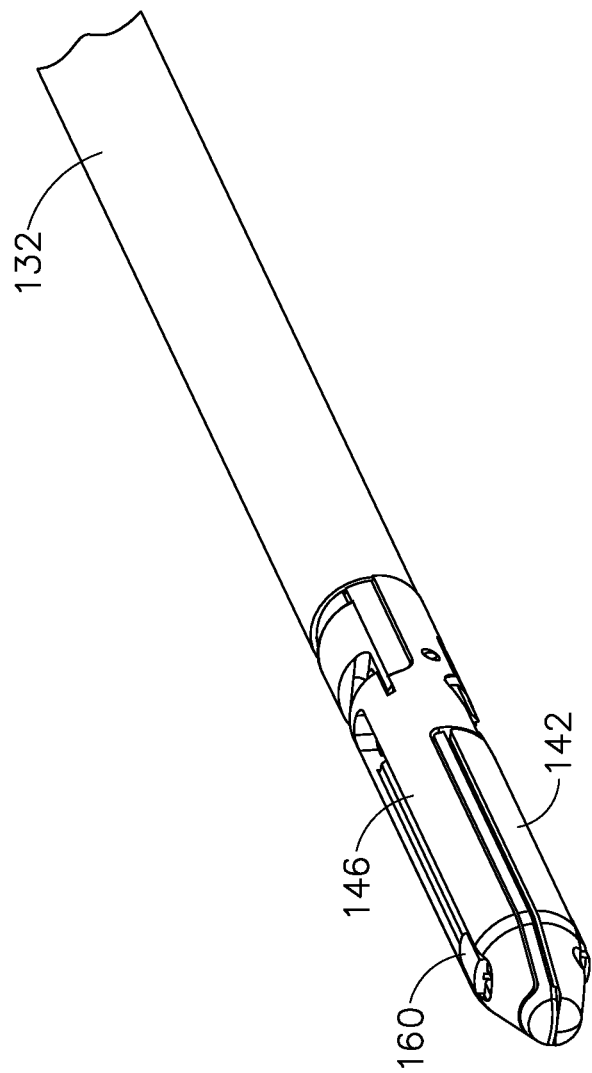
FIG. 22 depicts a perspective view of the end effector of FIG. 6 in the closed position with the firing beam advanced.

In some instances, instrument (10) is then used to advance firing beam (160) to sever tissue. Jaws (142, 144, 146) may be opened to the position shown in FIGS. 19B, 20B, and 21B by sliding second actuator (124) distally and jaws (142, 144, 146) may be positioned around two layers of tissue. Jaws (142, 144, 146) may then be closed to capture the two layers of tissue between jaws (142, 144, 146) by translating second actuator (124) proximally. With tissue captured between jaws (142, 144, 146), first actuator (122) may then be slid distally to thereby translate first translating member (134) and firing beam (160) distally, as shown in FIG. 22. As firing beam (160) advances, upper flange (162) slides within channels (153) of upper jaws (144, 146) to maintain the lateral position of upper jaws (144, 146). With tissue layers captured between jaws (142, 144, 146), distal blade (164) of firing beam (160) severs the clamped tissue layers and electrode surfaces (150, 152) are activated with bipolar RF energy by the user depressing activation button (26). Thus, a bipolar RF current flows between firing beam (160) and electrode surfaces (150, 152) of jaws (142, 144, 146), through the compressed regions of severed tissue layer portions to thermally weld the tissue layer portions on one side of firing beam (160) together and the tissue layer portions on the other side of firing beam (160) together.

In some instances, instrument (10) is used only to dissect tissue. In other instances, instrument (10) is used only to sever tissue. In other instances, instrument (10) is used to dissect tissue before and/or after severing tissue. In some instances, actuators (122, 124) are removed from shaft assembly (130) such that firing beam (160) may be advanced and/or retracted to close and/or open jaws (142, 144, 146). For instance, trigger (24) may be squeezed toward pistol grip (22) to advance firing beam (160). As firing beam (160) advances, flanges (162, 166) of firing beam (160) may cammingly act to pivot upper jaws (144, 146) inwardly toward each other and toward lower jaw (142). Trigger (24) may then be pivoted away from pistol grip (22) to retract firing beam (160). As firing beam (160) retracts, upper jaws (144, 146) may then pivot away from lower jaw (142) and outwardly away from each other to the open position. In some instances, fins (159) of upper jaws (144, 146) are removed such that upper jaws (144, 146) immediately pivot outwardly away from each other as upper jaws (144, 146) begin to pivot away from lower jaw (142). Other suitable methods of opening jaws (142, 144, 146) will be apparent to one with ordinary skill in the art in view of the teachings herein.

III. Miscellaneous

It should be understood that any of the versions of electrosurgical instrument (10) described herein may include various other features in addition to or in lieu of those described above. By way of example only, any of the devices herein may also include one or more of the various features disclosed in any of the various references that are incorporated by reference herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

In versions where the teachings herein are applied to a surgical stapling instrument, it should be understood that the teachings herein may be combined with the teachings of one or more of the following, the disclosures of all of which are incorporated by reference herein: U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, now U.S. Pat. No. 8,408,439, issued Apr. 2, 2013; and U.S. Pub. No. 2012/0239012, entitled "Motor-Driven Surgical Cutting Instrument with Electric Actuator Directional Control Assembly," published Sep. 20, 2012, now U.S. Pat. No. 8,453,914, issued Jun. 4, 2013. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising an end effector, wherein the end effector comprises:
    (a) a first jaw having a first electrode surface; and
    (b) a second jaw pivotable relative to the first jaw, wherein the second jaw is pivotable along a first plane from a closed position to a first open position, wherein the second jaw has a second electrode surface configured to cooperate with the first electrode surface to provide radiofrequency (RF) energy to tissue when the first and second jaws are in the closed position, wherein the second jaw comprises:
        (i) a first portion, and
        (ii) a second portion, wherein the second portion is pivotable relative to the first portion;
        wherein the second portion is configured to be positioned adjacent to the first portion of the second jaw when the second jaw is in the closed position;
        wherein the first and second portions of the second jaw are configured to pivot outwardly along respective paths that are transverse to the first plane as second jaw is pivoted from the closed position to the first open position.

2. The apparatus of claim 1, wherein the second jaw is pivotable along the first plane to a second open position, wherein the second open position is positioned between the closed position and the first open position, wherein the second portion of the second jaw is configured to remain adjacent to the first portion of the second jaw when the second jaw pivots along the first plane from the closed position to the second open position.

3. The apparatus of claim 2, wherein the first and second portions of the second jaw each comprise a fin, wherein the first jaw comprises a recess, wherein the fins of the first and second portions are insertable within the recess of the first jaw.

4. The apparatus of claim 3, wherein the fins of the first and second portions of the second jaw are configured to be positioned within the recess of the first jaw when the second jaw is pivoted from the closed position to the second open position.

5. The apparatus of claim 4, wherein the fins of the first and second portions of the second jaw are configured to be positioned out of the recess of the first jaw when the second jaw is pivoted from the second open position to the first open position.

6. The apparatus of claim 3, wherein the fins of the first and second portions of the second jaw each comprise a ramped surface.

7. The apparatus of claim 1, wherein the first jaw comprises a ramped surface, wherein the second jaw comprises a ramped surface that corresponds to the ramped surface of the first jaw, wherein the ramped surface of the second jaw is configured to cammingly engage the ramped surface of the first jaw when the second jaw is pivoted from the first open position to the closed position.

8. The apparatus of claim 1, wherein the second jaw comprises a tip feature, wherein the tip feature protrudes transversely across a distal end of the second jaw.

9. The apparatus of claim 1, wherein the end effector comprises a firing beam translatable relative to the first and second jaws.

10. The apparatus of claim 9, wherein the firing beam is operable to pivot the second jaw relative to the first jaw.

11. The apparatus of claim 9, wherein the firing beam comprises a flange, wherein the flange has a curved profile.

12. The apparatus of claim 11, wherein the second jaw defines a channel extending longitudinally along the second jaw, wherein the channel of the second jaw is configured to receive the curved flange of the firing beam, wherein the curved flange is configured to hold the first and second portions of the second jaw adjacently together when the firing beam is in a distal position.

13. The apparatus of claim 1, wherein the end effector comprises a slider translatable relative to the first jaw.

14. The apparatus of claim 13, wherein the slider defines a pair of openings, wherein the first and second portions of the second jaw each comprise a protrusion, wherein the protrusions of the first and second portions of the second jaw are positioned within the openings of the slider.

15. The apparatus of claim 14, wherein the slider defines a longitudinal axis, wherein the openings of the slider are oriented along opposing oblique angles relative to the longitudinal axis of the slider, wherein the oblique orientations of the openings are configured to enable pivoting of the first and second portions of the second jaw in two directions.

16. The apparatus of claim 14, wherein the slider is operable to pivot the second jaw relative to the first jaw.

17. The apparatus of claim 1 further comprising a first actuator, wherein the first actuator is operable to pivot the second jaw relative to the first jaw.

18. The apparatus of claim 17 further comprising a second actuator, wherein the end effector comprises a firing beam translatable relative to the first and second jaws, wherein the second actuator is operable to translate the firing beam.

19. An apparatus for operating on tissue, the apparatus comprising an end effector, wherein the end effector comprises:
(a) a first jaw having a first electrode surface; and
(b) a second jaw pivotable relative to the first jaw, wherein the second jaw comprises:
(i) a first portion, and
(ii) a second portion, wherein the second portion is pivotable relative to the first portion;
wherein the second jaw is pivotable relative to the first jaw along a first plane from a closed position to a first open position, wherein the second jaw has a second electrode surface configured to cooperate with the first electrode to provide radiofrequency (RF) energy to tissue when the first and second jaws are in the closed position, wherein the second jaw is further pivotable from the first open position to a second open position;
wherein the second portion of the second jaw is configured to be adjacent to the first portion of the second jaw when the second jaw is in the first open position;
wherein the second portion of the second jaw is configured to be positioned away from the first portion of the second jaw and laterally away from the first plane along respective paths that are transverse to the first plane when the second jaw is in the second open position.

20. An apparatus for operating on tissue, the apparatus comprising an end effector, wherein the end effector comprises:
(a) a first jaw having a first electrode surface;
(b) a second jaw pivotable relative to the first jaw, wherein the second jaw comprises:
(i) a first portion, and
(ii) a second portion, wherein the second portion is pivotable relative to the first portion; and
(c) a firing beam translatable relative to the first and second jaws;
wherein the second jaw is pivotable relative to the first jaw along a first plane from a closed position to an open position, wherein the second jaw has a second electrode surface configured to cooperate with the first electrode surface to provide radiofrequency (RF) energy to tissue when the first and second jaws are in the closed position, wherein the first and second portions of the second jaw are configured to pivot outwardly along respective paths that are transverse to the first plane after the second jaw has reached the open position;
wherein the firing beam is operable to pivot the second jaw relative to the first jaw along the first plane.

* * * * *